United States Patent [19]

Teutsch et al.

[11] Patent Number: 4,519,946
[45] Date of Patent: May 28, 1985

[54] STEROIDS

[75] Inventors: Jean G. Teutsch, Pantin; Germain Costerousse, Saint-Maurice; Daniel Philibert, La Varenne Saint Hilaire; Roger Deraedt, Pavillons sous Bois, all of France

[73] Assignee: Roussel Uclaf, Paris, France

[21] Appl. No.: 614,440

[22] Filed: May 25, 1984

Related U.S. Application Data

[60] Division of Ser. No. 595,267, Mar. 30, 1984, abandoned, which is a division of Ser. No. 386,967, Jun. 10, 1982, abandoned, which is a continuation-in-part of Ser. No. 338,077, Jan. 9, 1982, Pat. No. 4,386,085.

[30] Foreign Application Priority Data

Jan. 9, 1981 [FR] France .................. 81 00272

[51] Int. Cl.³ .............................. C07J 53/00
[52] U.S. Cl. ............... 260/239.55 R; 260/397.45; 260/397.1; 260/239.5
[58] Field of Search ........... 260/239.55 R, 397.45, 260/239.5

[56] References Cited

U.S. PATENT DOCUMENTS 4,386,085 5/1983 Teutsch et al. ............ 260/239.55 R

Primary Examiner—Albert L. Roberts
Attorney, Agent, or Firm—Charles A. Muserlian

[57] ABSTRACT

Novel 19-nor steroids and 19-nor-D-homo-steroids of the formula

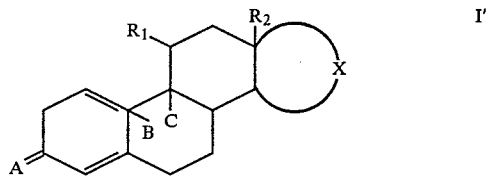

wherein $R_1$ is an organic radical of 1 to 18 carbons atoms containing at least one atom selected from the group consisting of nitrogen, phosphorous and silicon with the atom immediately adjacent to the 11-carbon atom being carbon, $R_2$ is a hydrocarbon of 1 to 8 carbon atoms, X is selected from the group consisting of a pentagonal ring and a hexagonal ring optionally substituted and optionally containing a double bond, B and C together form a double bond or an epoxy group, the C=A group at position 3 is selected from the group consisting of C-O, ketal, which may be open or closed

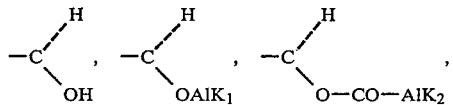

$-C=NOH, -C-NOAlK_3$ and $C-CH_2,AlK_1$, $AlK_2$ and $AlK_3$ are selected from the group consisting of alkyl of 1 to 8 carbon atoms and aralkyl of 7 to 15 carbon atoms and their non-toxic, pharmaceutically acceptable acid addition salts having anti-glucocoritcoid activity and a process for their preparation.

7 Claims, No Drawings

STEROIDS

PRIOR APPLICATION

This application is a division of U.S. patent application Ser. No. 595,267 filed Mar. 30, 1984 now abandoned which is a division of U.S. patent application Ser. No. 386,967 filed June 10, 1982 now abandoned which is a continuation-in-part of copending commonly assigned U.S. patent application Ser. No. 338,077 filed Jan. 9, 1982, now U.S. Pat. No. 4,386,085.

STATE OF THE ART

U.S. Pat. No. 4,233,296 describes steroids being substituted in the 11-position with substituents other than the present formula which require an organic substituent containing a nitrogen, phosphorous or silicon atom. U.S. Pat. No. 3,190,796 describes steroids having in a hydroxyl in the 11β-position. Schonemann et al European Journal of Medicin Chemistry, Chimica Therapeutica, Vol. 15, No. 4, (July, Aug. 1980), p. 333–335] describes steroids substituted in the 11β-position with

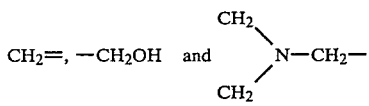

OBJECTS OF THE INVENTION

It is an object of the invention to provide the novel steroids of formula I and their non-toxic, pharmaceutically acceptable acid addition salts and a novel process and novel intermediates for their preparation.

It is another object of the invention to provide novel antiglucocorticoid compositions and to a novel method of inducing antiglucocorticoidal activity in warm-blooded animal.

These and other objects and advantages of the invention will become obvious from the following detailed description.

THE INVENTION

The novel steroids of the invention are selected from the group consisting of 19-nor steroids and 19-nor-D-homo-steroids of the formula

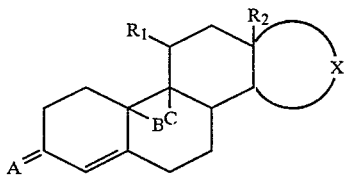

wherein $R_1$ is an organic radical of 1 to 18 carbon atoms containing at least one atom selected from the group consisting of nitrogen, phosphorous and silicon with the atom immediately adjacent to the 11-carbon atom being carbon, $R_2$ is a hydrocarbon on 1 to 8 carbon atoms, X is selected from the group consisting of a pentagonal ring and a hexagonal ring optionally substituted and optionally containing a double bond, B and C together form a double bond or an epoxy group, the C=A group at position 3 is selected from the group consisting of C=O ketal, which may be open or closed—

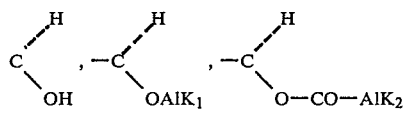

—C=NOH, —C=NOAlK$_3$ and C=CH$_2$, AlK$_1$, AlK$_2$ and AlK$_3$ are selected from the group consisting of alkyl of 1 to 8 carbon atoms and aralkyl of 7 to 15 carbon atoms and their non-toxic, pharmaceutically acceptable acid addition salts.

Preferably $R_2$ is a saturated alkyl of 1 to 4 carbon atoms such as methyl, ethyl, n-propyl or butyl and AlK$_1$, AlK$_2$ and AlK$_3$ are preferably methyl, ethyl, n-propyl, isopropyl or benzyl. X is preferably an optionally substituted remainder of a pentagonal ring.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, aryl sulfonic acids such as benzene sulfonic acid and p-toluene sulfonic acid and arylcarboxylic acid.

A preferred group of compounds are those of the formula

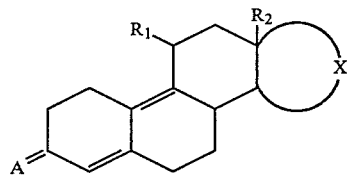

wherein $R_1$, $R_2$, A and X have the above definitions and their non-toxic, pharmaceutically acceptable acid addition salts.

Preferred compounds of formula I' are those wherein $R_2$ is methyl, those wherein X is the remainder of the pentagonal ring

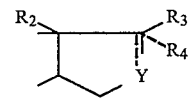

wherein $R_2$ has the above definition, the dotted line in the 16,17-position is an optional double bond, Y is the group

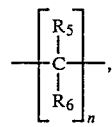

n is 1 or 2, $R_5$ is selected from the group consisting of hydrogen alkyl of 1 to 8 carbon atoms, alkenyl and alkynyl of 2 to 8 carbon atoms, aryl of 6 to 14 carbon atoms and aralkyl of 7 to 15 carbon atoms, $R_6$ may be the same as $R_5$ and may be selected from the same group of members as $R_5$ or —OH, $R_3$ and $R_4$ are individually selected from the group consisting of hydrogen, —OH, —OAlK$_4$, —OCOAlK$_5$, alkenyl and alkynyl of 2 to 8 carbon atoms,

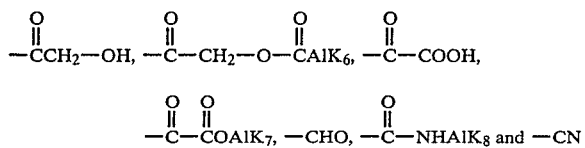

wherein AlK$_4$, AlK$_5$ and AlK$_8$ are selected from the group consisting of alkyl of 1 to 8 carbon atoms and aralkyl of 7 to 15 carbon atoms, AlK$_6$ is selected from the group consisting of optionally substituted alkyl of 1 to 8 carbon atoms and aralkyl of 7 to 15 carbon atoms and AlK$_7$ is alkyl of 1 to 8 carbon atoms and R$_3$ and R$_4$ form the group

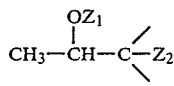

and Z$_1$ is selected from the group consisting of hydrogen, alkyl of 1 to 8 carbon atoms and acyl of an organic carboxylic acid of 1 to 8 carbon atoms and Z$_2$ is alkyl of 1 to 8 carbon atoms and those where R$_5$ is different from R$_6$.

When R$_5$ or R$_6$ are alkyl, they are preferably methyl or ethyl and when they are alkenyl or alkynyl, they are vinyl, isopropenyl, allyl, ethynyl or propynyl. When R$_5$ and R$_6$ are aryl or aralkyl, they are phenyl or benzyl.

When R$_3$ or R$_4$ are

are preferably methyl, ethyl, n-propyl, butyl, pentyl, hexyl or benzyl. When R$_3$ or R$_4$ are alkenyl or alkynyl, they are preferably vinyl, isopropenyl, allyl or 2-methylallyl or ethynyl or —C≡C—AlK$_9$ where AlK$_9$ is methyl, ethyl, propyl, isopropyl, isopropenyl, butyl, benzyl or CF$_3$—, AlK$_6$, AlK$_7$ or AlK$_8$ have preferably the same values as AlK$_4$ and AlK$_5$. The groups R$_3$ and R$_4$ are preferably different except where R$_3$ or R$_4$ each are hydrogen.

Among the preferred values of

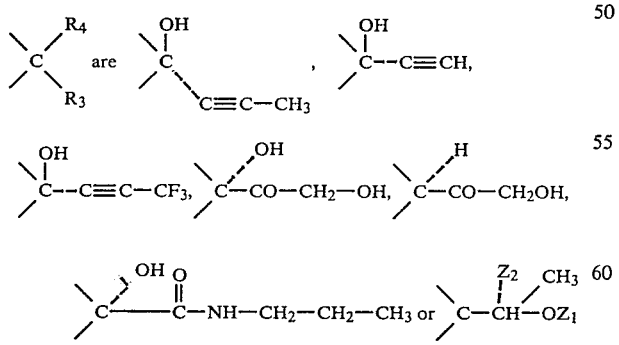

wherein Z$_1$ is hydrogen, alkyl of 1 to 8 carbon atoms or acyl of a hydrocarbon of 2 to 8 carbon atoms such as acetyloxy or benzoyl and Z$_2$ is alkyl of 1 to 8 carbon atoms such as methyl.

Other preferred compounds of formula I' are those wherein the D ring does not contain any ethylenic unsaturation, R$_5$ and R$_6$ are hydrogen, n is 1 and those compounds wherein =A is =O as well as those wherein R$_1$ is a hydrocarbon of 1 to 18 carbon atoms containing a nitrogen atom.

Especially preferred are the compounds of formula I' wherein R$_1$ is a primary, secondary or tertiary alkyl of 1 to 8 carbon atoms containing at least one heteroatom of the group consisting of oxygen, nitrogen and sulfur at least one of which is nitrogen or is substituted with a nitrogen heterocycle. Examples of alkyl are methyl, ethyl, n-propyl, isopropyl, butyl, isobutyl, tert.-butyl, pentyl, hexyl and cycloalkyl such as cyclopropyl, cyclobutyl, cyclopentyl or cyclohexyl. Examples of heterocycle containing a nitrogen atom are 3-pyridyl, 4-pyridyl, 2-pyridyl, thiazolyl and piperidinyl, Equally preferred are compounds of formula I' wherein R$_1$ is a heterocycle containing at least one nitrogen atom optionally substituted with alkyl of 1 to 8 carbon atoms.

Other preferred compounds of formula I' are those wherein R$_1$ is aryl or aralkyl substituted with a group

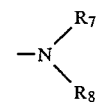

wherein R$_7$ and R$_8$ are alkyl of 1 to 8 carbon atoms or primary, secondary or tertiary alkyl of 1 to 8 carbon atoms containing at least one heteroatom of the group consisting of nitrogen, sulfur or oxygen of which at least one is nitrogen or a heterocycle containing at least one nitrogen atom. Examples of alkyl are those mentioned above as preferred and aryl or aralkyl are preferably phenyl or benzyl and the preferred heterocycles are those mentioned above. Especially preferred are those wherein R$_1$ is 2-pyridyl, 3-pyridyl, 4-pyridyl,

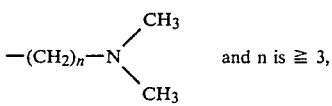

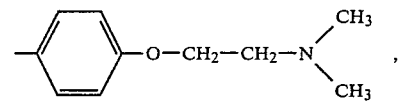

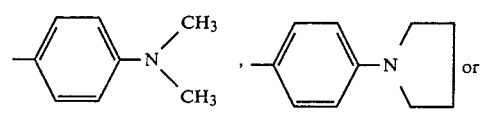

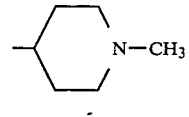

and especially those wherein R$_1$ is

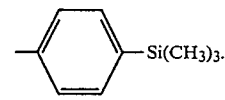

Among other preferred compounds are those wherein $R_1$ is a nitrogen oxide as well as those wherein B and C form an epoxy. Especially preferred compounds are those of Examples 1,3,4,8,10,11,12,14,16,17,20,22,28 and 29.

The novel process of the invention for the preparation of compounds of formula I' comprises reacting a compound of the formula

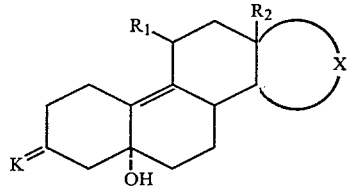
II wherein K is a ketone blocked in the form of a ketal, thioketal, oxime or methyloxime and $R_1$, $R_2$ and X have the above definitions with a dehydration agent capable of freeing the ketone group to form a compound of the formula

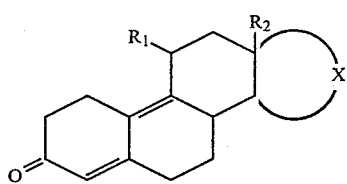
$I_A'$ and either reacting the latter with a ketalization agent to obtain a compound of the formula

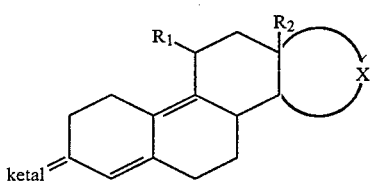
$I_B'$ or reacting the compound of formula $I_A'$ with $NH_2OH$ or $NH_2OAlK_3$ wherein $AlK_3$ has the above definition to obtain a compound of the formula

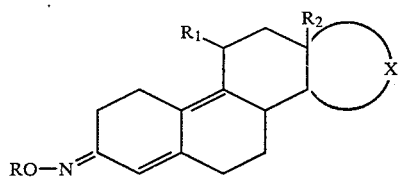
$I_C'$ wherein R is hydrogen or $AlK_3$ or reacting a compound of formula $I_A'$ with a reducing agent capable of selectively reducing the 3-keto group to obtain a compound of the formula

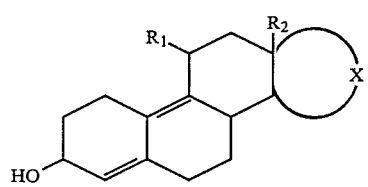
$I_D'$ and reacting the latter with an etherification agent capable of introducing $AlK_1$ to obtain a compound of the formula

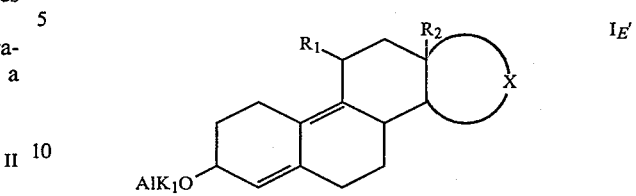
$I_E'$ or reacting the compound of formula $I_D'$ with an esterification agent capable of introducing $COAlK_2$ to obtain a compound of the formula

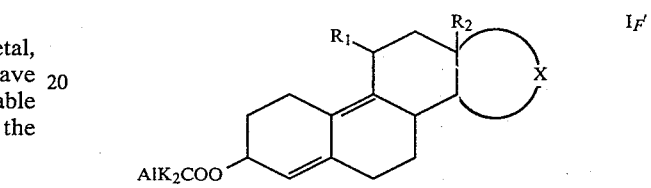
$I_F'$ or transforming the compound of formula $I_A'$ by known methods to a compound wherein C=A is $CH_2$ and reacting a compound of formula $I_A'$, $I_B'$, $I_C'$, $I_D'$, $I_E'$ or $I_F'0$ with an acid to form the corresponding acid addition salt or with an oxidation agent to obtain when $R_1$ is a radical containing a nitrogen atom a compound having in the 11β-position a radical wherein the nitrogen atom is in the oxide form and B and C optionally form an epoxide bridge or when $R_1$ does not contain a nitrogen atom, a compound where B and C form an epoxide bridge and when the compound contains the nitrogen oxide and the B and C group form an epoxide bridge, selectively reducing the oxidized nitrogen atom in $R_1$ and optionally reacting the latter with an acid to form the acid addition salt.

The process of the invention is particularly useful for forming products of formula I' wherein X form a pentagonal ring of the formula

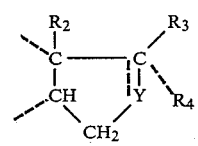

wherein $R_2$, $R_3$, $R_4$, Y and the dotted line in the 16,17-position have the above definition.

In a preferred mode of the process of the invention, the dehydration agent capable of freeing the ketone group is a sulfonic acid resin in the acid form such as a commercial sulfonic acid resin based on polystyrene or a styrene-divinyl-benzene polymer but equally useful are inorganic acids such as sulfuric acid or hydrochloric acid in a lower alkanol or perchloric acid in acetic acid or a sulfonic acid such as p-toluene sulfonic acid.

The ketalization agent is preferably an alcohol or a dialcohol in the presence of an organic acid such as oxalic acid or p-toluene sulfonic acid. The agent for reducing the ketone group is preferably an alkali metal hydride as discussed by Walkis [Chemical Society Review, Vol. 5, No. 1 (1976), p. 23]. The etherification agent is preferably an alkyl halide in the presence of a base and the esterification agent is preferably a carboxylic acid derivative such as the acid anhydride or acid chloride in the presence of a base such as pyridine.

It goes without saying that when one of $R_3$ or $R_4$ in the compounds of formula I' obtained above is —OH, the compounds of formula I' may be reacted with an etherification agent or an esterification agent which is one of those discussed above. When $R_3$ or $R_4$ is a 17-acyloxy, the compound may be optionally saponified with a saponification agent such as a base like sodium hydroxide, potassium hydroxide, potassium amide or potassium tert.-butylate and the reaction is preferably effected in a lower alkanol such as ethanol or methanol but equally useful is lithium acetylide in ethylenediamine.

The oxidation agent is preferably a peracid such as m-chloroperbenzoic acid, peracetic acid or perphthalic acid or hydrogen peroxide alone or in the presence of hexachloroacetone or hexafluoroacetone. When it is desired to obtain a compound in which the nitrogen atom of $R_1$ is oxidized, one uses an equivalent of the oxidation agent and when it is desired to obtain a compound in which B and C form an epoxide bridge, two equivalents of agent are used. The selective reducing agent for the N-oxide is preferably triphenylphosphine and operating for example with acetic acid.

Another object of the invention is a process for the preparation of the compounds of formula II wherein a compound of the formula

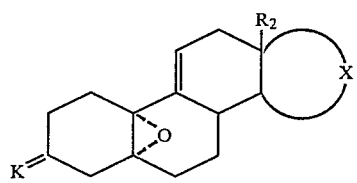

III is reacted with a compound selected from the group consisting of $LiCu(R_1)_2$, $LiR_1$ and $R_1MgHal$ wherein $R_1$ has the above definition and Hal is halogen in the presence of a cuprous halide. In a preferred mode of the said process, the reaction is effected at room temperature and the reactant is $R_1MgHal$ in the presence of a cuprous salt.

Another object of the invention is a process for the preparation of a compound of the formula

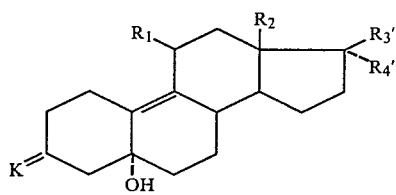

II' wherein $R_1$, $R_2$ and K have the above definitions, $R_3'$ is selected from the group consisting of —OH and $OR_c$, $R_c$ is the residue $AlK_4$ of an ether group or $COAlK_5$ of an ester group and $R_4'$ is hydrogen or alkenyl or alkynyl of 2 to 8 carbon atoms comprising reacting a compound of the formula

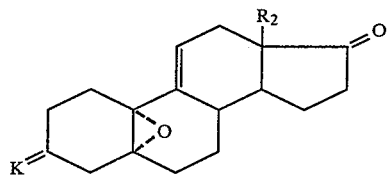

IV with a compound selected from the group consisting of $LiCu(R_1)_2$, $R_1Li$ and $R_1MgHal$ in the presence of a cuprous halide to obtain a compound of the formula

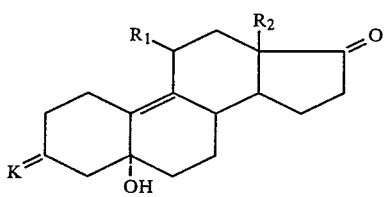

V and either reducing the latter to obtain the corresponding 17-ol compound or with an appropriate magnesium to obtain the corresponding 17α-substituted-17β-ol steroid or with an organometallic derivative such as a lithium or potassium derivative to obtain the corresponding 17α-substituted-17β-ol steroid or with a cyanuration agent to obtain the corresponding 17α-ol-17β-cyano steroid, protecting the hydroxy group and reacting the latter with an organometallic compound as discussed above to obtain the corresponding 17α-substituted-17β-ol steroid and in the case of one of the compounds obtained is 17-hydroxylated, reacting it with an etherification agent or esterification agent and in the case when one of the compounds contains a 17 substituent with a triple bond reacting the latter with a reducing agent to obtain the corresponding ethylenic derivative.

In a preferred mode of the latter process, the reaction of the compound of formula IV with a compound of the group consisting of $R_1Li$, $LiCu(R_1)_2$ or $R_1MgHal$ is effected under the previously described conditions. The different reactants for reaction with the compounds of formula V are known in steroid chemistry and are illustrated in the specific examples.

The novel intermediates of the invention are the compounds of formula II and V. Particularly preferred compounds of the invention are 3,3-[1,2-ethanediyl bisoxy]-11β-[4-trimethylsilyl-phenyl]-17α-(prop-1-ynyl)-Δ⁹-estrene-5α,17β-diol, 3,3-[1,2-ethanediyl-bisoxy]-11β-(4-pyridyl)-17α-(prop-1-ynyl)-Δ⁹-estrene-5α,17β-diol, 3,3-[1,2-ethanediyl-bisoxy]-11β-[3-(N,N-dimethylamino)-propyl]-17α-(prop-1-ynyl)-Δ⁹-estrene-5α,17β-diol, 3,3-[1,2-ethanediyl-bisoxy]-11β-[4-(N,N-dimethylamino)-phenyl]-17α-(prop-1-ynyl)-Δ⁹-estrene-5α,17β-diol, 3,3-[1,2-ethanediyl-bisoxy]-11β-[4-(N,N-dimethylaminoethoxy)phenyl]-17α-(prop-1-ynyl)-Δ⁹-estrene-5α,17β-diol, 3,3-[1,2-ethanediyl-bisoxy]-11β-[4-(N,N-dimethylamino)-phenyl]-21-chloro-19-nor-17α-Δ⁹-pregnene-20-yne-5α,17β-diol and 3,3-[1,2-ethanediyl-bisoxy]-11β-[4-(N,N-dimethylamino)-phenyl]-17α-(prop-2-ynyl)-Δ⁹-estrene-5α,17β-diol.

The compounds of formula III and especially of formula IV used to prepare the compounds of formula II or V are generally known compounds which can be prepared by reacting the corresponding Δ⁵⁽¹⁰⁾,⁹⁽¹¹⁾ steroids with an epoxidation agent selective for the 5(10)

double bond, for example with hydrogen peroxide in the presence of hexachloroacetone or hexafluoroacetone as described in French Pat. No. 2,423,486. The new compound, 3,3-[1,2-ethanediyl-bisoxy]-17α-(prop-1-ynyl-5α,10α-epxoy-Δ$^{9(11)}$-estrene-17β-ol is prepared in the Example.

The following compounds are compounds falling within the scope of the invention:
(A) compounds of the formula

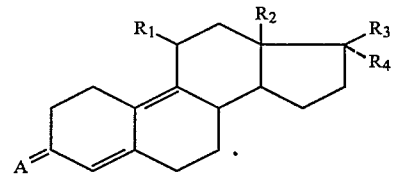

10 wherein the A, $R_1$, $R_2$, $R_3$ and $R_4$ substitutes are indicated in Table I

| A | $R_1$ | $R_2$ | $R_3$ | $R_4$ |
|---|---|---|---|---|
| O | ![N-ethyl-N-methyl-phenyl] | $CH_3$ | OH | —C≡C—H |
| " | " | " | " | —C≡C—$CF_3$ |
| " | " | " | " | —C≡C—$CH_2CH_3$ |
| " | " | " | " | —$CH_2$—C≡C—H |
| " | " | " | " | —C≡C—$SiMe_3$ |
| " | " | " | —C≡C—H | OH |
| " | " | " | —C≡C—$SiMe_3$ | OH |
| " | " | $CH_2CH_3$ | OH | —C≡C—H |
| " | " | " | OH | —C≡C—$CH_3$ |
| " | " | " | OH | —$CH_2$—C≡C—H |
| " | " | $CH_3$ | —C(=O)—$CH_2OH$ | H |
| " | " | " | " | OH |
| HO—N=(E) | " | " | OH | —C≡C—H |
| " | " | " | " | —C≡C—$CH_3$ |
| " | " | " | —C≡C—H | OH |
| " | " | " | OH | —$CH_2$—C≡C—H |
| HO—N=(Z) | " | " | OH | —C≡C—H |
| " | " | " | " | —C≡C—$CH_3$ |
| " | " | " | " | —$CH_2$—C≡C—H |
| " | " | " | —C≡C—H | OH |
| O | ![indoline] | " | OH | —C≡C—H |
| " | " | " | " | —C≡C—$CF_3$ |
| " | " | " | " | —$CH_2$—C≡C—H |
| " | " | " | " | —C≡C—$CH_2CH_3$ |
| " | " | " | " | —C≡C—Cl |
| " | " | " | " | —C≡C—$SiMe_3$ |
| " | " | " | —C≡C—H | OH |
| " | " | " | —C≡C—$SiMe_3$ | OH |
| " | " | " | " | —C≡C—H |
| " | " | " | " | —C≡C—$CH_3$ |
| " | " | " | " | —$CH_2$—C≡C—H |
| " | " | $CH_3$ | —C(=O)—$CH_2OH$ | —H |
| " | " | " | " | —OH |
| " | " | " | —C(=O)—$CH_3$ | —H |
| HO—N=(E) | " | " | —OH | —C≡C—H |
| " | " | " | " | —C≡C—$CH_3$ |
| " | " | " | " | —C≡C—$CH_2CH_3$ |
| " | " | " | " | —$CH_2$—C≡C—H |
| " | " | " | —C≡C—H | —OH |
| " | " | " | —C(=O)—$CH_2OH$ | H |

-continued

| A | R₁ | R₂ | R₃ | R₄ |
|---|---|---|---|---|
| HO—N=(Z) | " | " | " | " |
| " | " | " | OH | —C≡C—H |
| " | " | " | " | —C≡C—CH₃ |
| " | " | " | " | —C≡C—CH₂CH₃ |
| " | " | " | " | —CH₂—C≡C—H |
| " | " | " | —C≡C—H | —OH |
| O←N(—CH₂—phenyl-CH₃) | " | " | " | " |
| " | " | " | OH | —C≡C—H |
| " | " | " | " | —C≡C—CF₃ |
| " | " | " | " | —C≡C—Cl |
| " | " | " | " | —C≡C—CH₂CH₃ |
| " | " | " | " | —CH₂—C≡C—H |
| " | " | " | " | —C≡C—SiMe₃ |
| " | " | " | —C(=O)—CH₂OH | —H |
| HO—N=(E) | " | " | OH | —C≡C—H |
| " | " | " | " | —C≡C—CH₃ |
| " | " | " | " | —CH₂—C≡C—H |
| " | " | " | —C≡C—H | —OH |
| HO—N=(Z) | " | " | " | " |
| " | " | " | OH | —C≡C—H |
| " | " | " | " | —C≡C—CH₃ |
| " | " | " | " | —CH₂—C≡C—H |
| O, (CH₃)₂N—phenyl- | " | " | " | —C≡C—CH₂CH₃ |
| " | " | " | " | —C≡C—CF₃ |
| " | " | " | —C≡C—SiMe₃ | —OH |
| " | " | " | —C(=O)—CH₂OH | —H |
| " | " | " | " | —OH |
| " | " | " | —C(=O)—CH₃ | —H |
| " | " | CH₂CH₃ | OH | —C≡C—H |
| " | " | " | —C≡C—CH₃ | " |
| " | " | " | " | —C≡C—Cl |
| " | " | " | " | —C≡C—CH₂—CH₃ |
| " | " | " | " | —C≡C—SiMe₃ |
| " | " | " | " | —CH₂—C≡C—H |
| " | " | " | —C(=O)—CH₂OH | —H |
| HO—N=(E) | " | CH₃ | —C≡C—H | —OH |
| " | " | " | —C(=O)—CH₂OH | —H |
| " | " | " | OH | —CH₂—C≡C—H |
| HO—N=(Z) | " | " | " | " |
| " | N-phenyl-CH₃ | " | —C≡C—H | —OH |

-continued

| A | R₁ | R₂ | R₃ | R₄ |
|---|---|---|---|---|
| " | " | " | $-\underset{\underset{O}{\|\|}}{C}-CH_2OH$ | —H |
| O | [4-(Me₂N⁺(–O⁻))–C₆H₄–] | " | " | " |
| " | " | " | " | —C≡C—H, —OH |
| " | " | " | OH | —CH₂—C≡C—H |
| " | " | " | " | —C≡C—CH₂CH₃ |
| " | " | " | " | —C≡C—CF₃ |
| " | " | " | " | —C≡C—H |
| " | " | " | " | —C≡C—SiMe₃ |
| HO—N=(E) | " | " | OH | —C≡C—H |
| " | " | " | " | —C≡C—CH₃ |
| " | " | " | " | —C≡C—CH₂CH₃ |
| " | " | " | " | —C≡C—Cl |
| " | " | " | " | —C≡C—SiMe₃ |
| " | " | " | " | —CH₂—C≡C—H |
| " | " | " | —C≡C—H | —OH |
| HO—N=(Z) | " | " | " | " |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —C≡C—SiMe₃ |
| " | " | " | " | —CH₂—C≡C—H |
| O | [4′-(Me₂N)–biphenyl-4-yl] | " | OH | —C≡C—H |
| " | " | " | " | —C≡C—CF₃ |
| " | " | " | " | —C≡C—CH₃ |
| " | " | " | " | —C≡C—Cl |
| " | " | " | " | —CH₂—C≡C—H |
| " | " | " | " | —H |
| " | " | " | —C≡C—H | —OH |
| " | " | " | $-\underset{\underset{O}{\|\|}}{C}-CH_2OH$ | —H |
| " | [4′-(Me₂N)–biphenyl-4-yl] | " | " | " |
| " | " | " | " | —C≡C—H |
| " | " | " | OH | —C≡C—H |
| " | " | " | " | —C≡C—CH₃ |
| " | " | " | " | —C≡C—Cl |
| " | " | " | " | —CH₂—C≡C—H |
| " | " | " | —C≡C—H | —OH |
| " | [4′-(O⁻←N⁺(Me)₂)–biphenyl-4-yl] | " | " | " |
| " | " | " | OH | —C≡C—H |
| " | " | " | " | —C≡C—CF₃ |
| " | " | " | " | —C≡C—CH₃ |
| " | " | " | " | —CH₂—C≡C—H |
| " | " | " | " | —H |
| " | [4-(Me₂N–CH₂CH₂–O)–C₆H₄–] | " | " | —C≡C—H |

-continued

| A | R₁ | R₂ | R₃ | R₄ |
|---|---|---|---|---|
| " | " | " | " | —CH₂—C≡C—H |
| " | " | " | —C≡C—H | —OH |
| " | " | " | O=C—CH₂OH (acetol group) | —H |
| " | 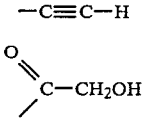 | " | " | " |
| " | " | " | —C≡C—H | —OH |
| " | " | " | —OH | —C≡C—H |
| " | " | " | " | —C≡C—CH₃ |
| " | " | " | " | —CH₂—C≡C—H |
| " | 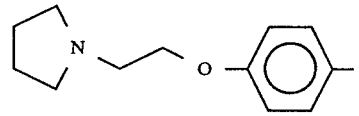 | " | —OH | —C≡C—H |
| " | " | " | " | —C≡C—CH₃ |
| " | " | " | " | —CH₂—C≡C—H |
| " | " | " | —C≡C—H | —OH |
| " | " | " | O=C—CH₂OH | —H |
| " | 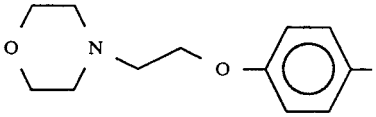 | " | " | " |
| " | " | " | —C≡C—H | OH |
| " | " | " | OH | —C≡C—CF₃ |
| " | " | " | OH | —C≡C—H |
| " | " | " | " | —CH₂—CH=CH₂ |
| " | " | " | " | CH₂—C≡C—H |
| " | " | " | " | —CH₂ |
| " | " | " | O=C—CH₃ | —CH₃ |
| " | " | " | " | " |
| HO—N=(E) | " | " | OH | —CH₂—CN |
| " | " | " | OH | —C≡C—H |
| " | " | " | " | —C≡C—CH₃ |
| " | " | " | " | —C≡C—CH₂CH₃ |
| " | " | " | " | —C≡C—Cl |
| " | " | " | " | —CH₂—C≡C—H |
| " | " | " | —C≡C—H | —OH |
| " | " | " | O=C—CH₂OH | —H |
| HO—N=(Z) | " | " | " | " |
| " | " | " | —C≡C—H | —OH |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —CH₂—C≡C—H |
| O | " | CH₂CH₃ | " | —C≡C—H |
| " | " | " | " | —C≡C—CH₃ |
| " | " | " | " | —CH₂—C≡C—H |
| " | " | " | " | —CH₂—CH=CH₂ |

-continued
| A | R₁ | R₂ | R₃ | R₄ |
|---|----|----|----|----|
| " | " | " | \C(=O)-CH₃ | -CH₃ |
| " | " | " | \C(=O)-CH₂OH | -H |
| " | " | " | -C≡C-H | -OH |
| " | 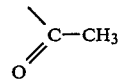 | CH₃ | OH | -C≡C-H |
| " | " | " | " | -C≡C-CH₃ |
| " | " | " | " | -C≡C-Cl |
| " | " | " | " | -C≡C-CH₂CH₃ |
| " | " | " | " | -CH₂-C≡C-H |
| " | " | " | " | -CH₂-CH=CH₂ |
| " | " | " | -C≡C-H | -OH |
| " | " | " | \C(=O)-CH₂OH | -H |
| " | " | " | \C(=O)-CH₃ | -CH₃ |
| " | " | " | \C(=O)-CH₃ | -H |
| " | 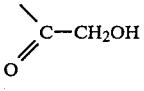 | " | " | " |
| " | " | " | " | -CH₃ |
| " | " | " | \C(=O)-CH₂OH | -H |
| " | " | " | -C≡C-H | -OH |
| " | " | " | OH | -C≡C-H |
| " | " | " | " | -C≡C-CH₃ |
| " | " | " | " | -C≡C-Cl |
| " | " | " | " | -C≡C-CH₂CH₃ |
| " | " | " | " | -CH₂-C≡C-H |
| " | " | " | " | -CH₂-CH=CH₂ |
| " | " | " | " | -C≡C-H |
| " | 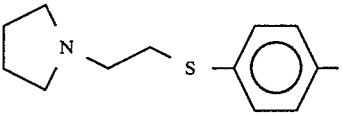 | " | " | " |
| " | " | " | -C≡C-H | -OH |
| " | " | " | \C(=O)-CH₂OH | -H |

-continued

| A | R₁ | R₂ | R₃ | R₄ |
|---|----|----|----|----|
| " | Me₃Si-CH₂-N(→O)(CH₃)-C₆H₄- (p-tolyl N-oxide) | " | OH | −C≡C−H |
| " | " | " | " | −C≡C−CH₃ |
| " | " | " | " | −CH₂−C≡C−H |
| " | " | " | −C≡C−H | −OH |
| " | " | " | O=C(·)−CH₂OH | −H |
| " | 1-(N,N-dimethylamino)-5-methylnaphthyl | " | OH | −C≡C−CH₃ |
| " | " | " | " | −CH₂−C≡C−H |
| " | " | " | " | −C≡C−H |
| " | 2-(N,N-dimethylamino)-6-methylnaphthyl | " | " | −C≡C−CH₃ |
| " | " | " | " | −C≡C−Cl |
| " | " | " | " | −CH₂−C≡C−H |
| " | " | " | −C≡C−H | −OH |
| " | " | " | " | −H, with O=C(·)−CH₂OH at R₃ |
| " | 2-(N,N-dimethylamino N-oxide)-6-methylnaphthyl | " | " | " |
| " | " | " | " | −C≡C−H ; −OH |
| " | " | " | " | −OH ; −C≡C−H |
| " | " | " | " | −C≡C−CH₃ |
| " | " | " | " | −C≡C−Cl |
| " | " | " | " | −CH₂−C≡C−H |
| " | Me₃SiCH₂− | " | " | −C≡C−H |
| " | " | " | " | −C≡C−CH₃ |
| " | " | " | " | −CH₂−C≡C−H |
| HO−N=(E) | " | " | −C≡C−H | −OH |
| " | " | " | OH | −C≡C−H |
| " | " | " | " | −C≡C−CH₃ |
| " | " | " | " | −CH₂−C≡C−H |
| HO−N=(Z) | " | " | −C≡C−H | −OH |
| " | " | " | OH | −C≡C−H |
| " | " | " | " | −C≡C−CH₃ |
| " | " | " | " | −CH₂−C≡C−H |
| O | (CH₃)₂N−CH₂CH₂CH₂−O−C₆H₄−(p-tolyl) | " | " | −C≡C−CH₃ |

-continued

| A | R₁ | R₂ | R₃ | R₄ |
|---|---|---|---|---|
| " | " | " | $\underset{O}{\overset{\parallel}{C}}-CH_2OH$ | —H |
| " | (CH₃)₂N-CH₂CH₂CH₂-S-C₆H₄- | " | " | " |
| " | " | " | OH | —C≡C—H |
| " | " | " | " | —C≡C—CH₃ |
| " | " | " | " | —CH₂—C≡C—H |
| " | " | " | " | —CH₂—CH=CH₂ |
| " | " | " | " | —CH₂CN |
| " | " | " | —C≡C—H | —OH |
| " | " | " | $\underset{O}{\overset{\parallel}{C}}-CH_2OH$ | —H |
| " | " | " | $O=\overset{\mid}{C}-CH_3$ | —CH₃ |
| " | " | " | OH | —H |
| " | (CH₃)₂N-CH₂CH₂-N(Me)-C₆H₄- | " | OH | —C≡C—H |
| " | " | " | " | —C≡C—CF₃ |
| " | " | " | " | —C≡C—CH₂CH₃ |
| " | " | " | " | —C≡C—Cl |
| " | " | " | " | —CH₂—C≡C—H |
| " | " | " | —C≡C—H | —OH |
| " | " | " | $\underset{O}{\overset{\parallel}{C}}-CH_2OH$ | —H |
| " | " | " | $\overset{O}{\overset{\parallel}{C}}-CH_3$ | —CH₃ |
| " | " | CH₂CH₃ | OH | —C≡C—H |
| " | " | " | " | —C≡C—CH₃ |
| " | " | " | " | —CH₂—C≡C—H |
| " | " | " | —C≡C—H | —OH |
| " | " | " | $\underset{O}{\overset{\parallel}{C}}-CH_2OH$ | —H |
| " | pyrrolidine-N-CH₂CH₂-N(Me)-C₆H₄- | CH₃ | OH | —C≡C—H |
| " | " | " | " | —C≡C—CH₃ |
| " | " | " | " | —CH₂—C≡C—H |
| " | " | " | —C≡C—H | —OH |
| " | " | " | $\underset{O}{\overset{\parallel}{C}}-CH_2OH$ | —H |

-continued

| A | R₁ | R₂ | R₃ | R₄ |
|---|----|----|----|----|
| " | Me—N(piperazine)—N—C₆H₄— | " | " | " |
| " | " | " | —C≡C—H | —OH |
| " | " | " | OH | —C≡C—H |
| " | " | " | " | —CH₂—C≡C—H |
| " | " | " | " | —CH₂—CH=CH₂ |
| " | " | " | " | —CH₂CN |
| " | Et—N(piperazine)—N—C₆H₄— | " | " | —C≡C—H |
| " | " | " | " | —C≡C—CH₃ |
| " | " | " | " | —CH₂—C≡C—H |
| " | " | " | " | —CH₂—CH=CH₂ |
| " | " | " | " | —CH₂—CN |
| " | " | " | —C≡C—H | —OH |
| " | " | " | —OH | —C≡C—H |
| " | Me-N-tetrahydroquinoline- | " | " | " |
| " | " | " | " | —C≡C—CH₃ |
| " | " | " | " | —CH₂—C≡C—H |
| " | " | " | —C≡C—H | —OH |
| " | " | " | >C(=O)—CH₂OH | —H |
| " | Me₂N—(CH₂)₃—N(Me)—C₆H₄— | " | " | " |
| " | " | " | —C≡C—H | OH |
| " | " | " | OH | —C≡C—H |
| " | " | " | " | —C≡C—CH₃ |
| " | " | " | " | —CH₂—C≡C—H |
| " | " | " | " | —H |
| " | " | " | " | —CH₃ |
| " | pyridazinyl-N—C₆H₄— | " | " | —C≡C—H |
| " | " | " | " | —C≡C—CH₃ |
| " | " | " | " | —C≡C—CF₃ |
| " | " | " | " | —CH₂—C≡C—H |
| " | " | " | —C≡C—H | —OH |
| " | (H₃C)(H₃C)N—C(=N—)S— (methylthiazole) | " | OH | —C≡C—H |
| " | " | " | " | —C≡C—CH₃ |
| " | " | " | " | —C≡C—CF₃ |
| " | " | " | " | —CH₂—C≡C—H |
| " | " | " | —C≡C—H | —OH |
| " | " | " | —C≡C—CH₃ | —OH |

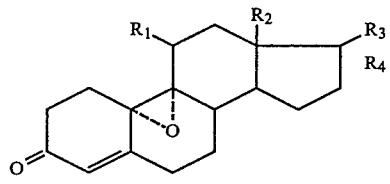

wherein $R_1$, $R_2$, $R_3$ and $R_4$ have the definitions in Table II

| $R_1$ | $R_2$ | $R_3$ | $R_4$ |
|---|---|---|---|
| ![Et,Me-N-phenyl] | CH₃ | OH | —C≡C—H |
| " | " | " | —C≡C—CH₃ |
| " | " | " | —C≡C—CF₃ |
| " | " | " | —CH₂CH₃ |
| " | " | " | —CH₂—C≡C—H |

| $R_1$ | $R_2$ | $R_3$ | $R_4$ |
|---|---|---|---|
| ![Et,Me-N-phenyl] | CH₃ | —C≡C—H | —OH |
| ![Me-N-indoline] | " | OH | —C≡C—H |
| " | " | " | —C≡C—CH₃ |
| " | " | " | —C≡C—CF₃ |
| " | " | " | —C≡C—CH₂CH₃ |
| " | " | " | —CH₂—C≡C—H |
| " | " | " | —H |
| " | " | " | —CH₂CH₃ |
| " | " | —C≡C—H | —OH |
| " | " | \—C(=O)—CH₂OH | —H |
| " | " | \—C(=O)—CH₃ | —CH₃ |
| ![Me-N(O)-indoline] | " | " | " |
| " | " | OH | —C≡C—H |
| " | " | " | —C≡C—CH₃ |
| " | " | " | —C≡C—CF₃ |
| " | " | " | —CH₂CH₃ |
| " | " | " | —CH₂—C≡C—H |
| " | " | —C≡C—H | —OH |
| " | " | OH | H |
| ![Me₂N-phenyl] | " | —C(=O)—CH₃ | CH₃ |
| " | " | OH | —C≡C—H |
| " | " | " | —C≡C—CH₃ |
| " | " | " | —C≡C—CF₃ |
| " | " | " | —CH₂CH₃ |
| " | " | " | —CH₂—C≡C—H |

-continued

| R₁ | R₂ | R₃ | R₄ |
|---|---|---|---|
| O=N(—)—⟨phenyl⟩— | " | OH | —C≡C—H |
| " | " | " | —C≡C—CH₃ |
| " | " | " | —C≡C—CF₃ |
| " | " | " | —CH₂—CH₃ |
| " | " | " | —CH₂—C≡C—H |
| " | " | " | H |
| " | " | " | CH₃ |
| " | " | —C≡C—H | OH |

Also prepared are the epoxides of the compounds of Table II.

The antiglucocorticoid compositions of the invention are comprised of an antiglucocorticoidally effective amount of at least one compound of formula I' and its non-toxic, pharmaceutically acceptable acid addition salts and an inert pharmaceutical carrier or excipient. The compositions may be in the form of tablets, dragees, gelules, granules, suppositories, injectable solutions or suspensions, pomades cremes and gels.

Examples of suitable excipients are talc, gum arabic lactose, starch, magnesium stearate, cocoa butter, aqueous or non-aqueous vehicles, fatty bodies of animal or vegetable origin, paraffinic derivatives, glycols, diverse wetting agents, dispersants or emulsifiers and preservatives.

The compositions of the invention have remarkable antiglucocorticoid properties as can be seen from the pharmalogical data infra. The study of the products against hormonal receptors shows that the compositions possess progestomimetic activity or anti-progestomimetic, androgenic or antiandrogenic activity.

The compositions are used principally against secondary effects of glucocorticoids and are equally useful against troubles due to a hypersecretion of glucocorticoids and especially against aging in general and are particularly active against hypertension, atherosclerosis, osteoporosis, diabetes, obesity as well as depression of immunity and insomnia. The compositions of the invention also possess antiprogestomimetic activity and are useful for the preparation of original contraceptives and are equally useful against hormonal irregularities and they present an interest in the treatment of hormonodependent cancers.

Some of the compounds of formula I' and their acid addition salts also possess progestomimetic activity and are useful for the treatment of amenorrhea, dysmenorrhea and luteal insufficiencies.

The compositions of the invention also present antiandrogenic activity making them useful for the treatment of hypertrophia, prostate cancer, hyperandrogenia, anemia, hirsutism and acne.

The novel method of the invention of inducing antigluocorticoid activity in warm-blooded animals, including humans, comprises administering to warm-blooded animals an antiglucocorticoidally effective amount of at least one compound of formula I' and their non-toxic, pharmaceutically acceptable acid addition salts. The usual daily dose is 0,15 to 15 mg/kg depending on the specific condition being treated and the compound used and the method of administration. The active compound may be administered orally, rectally, parenterally or locally.

In the following examples there are described several preferred embodiments to illustrate the invention. However, it is to be understood that the invention is not intended to be limited to the embodiments.

The antiprogestomimetic compositions of the invention contain a physiologically active quantity of at least one product of formula I and its pharmacutically acceptable acid addition salts as antiprogestomimetics.

These compositions may be administered via the digestive tract, parenterally or locally, particularly in the vagina or via the endonasal route. They may be in the form of a simple tablet or lozenges, gelatin capsules, granulated, suppositories, ovules, injectable preparations, ointments, creams or gels which are prepared according to the usual methods.

Excipients which may be employed are talc, gum arabic, lactose, starch, magnesium stearate, cocoa butter, animal and vegetable fats, paraffin derivatives, glycols, various wetting agents, dispersants, emulsifiers and preservatives.

The antiprogestomimetic compositions of the invention have remarkable properties as may be seen in the pharmacologicae tests which are described later.

The antiprogestomimetic compositions of the invention are used essentially to induce menses in female warm blooded animals.

The induction of menses during the luteal phase of the cycle and particularly at the end of the luteal phase permits the use of the compositions of the invention as contraceptives.

The antiprogrestomimetic compositions according to the invention may be equally used as agents to interrupt pregnancy since experiments with animals have demonstrated them to be abortive at any period of gestation.

The new method of the invention consists of inducing the menses in warm blooded female animals including women and is characterised in that one administers a quantity of antiprogestomimetic compound which is physiologically active such as a product of formula I'.

But it is understood that the essential role of progesterone is assigned during the luteal phase of the cycle at the moment of implantation of the embryo and during pregnancy.

The use of an antiprogestomimetic as an inducer of menstruation has been proposed, for example, in the tenth World Health Organization report page 80 and later in Chemtech, September 1977 page 566.

The method of utilization of this product is equally suggested as "post-coital and once-a-month drugs" in the report in WHO and in the expression "when taken monthly ... will induce menstruation" in the Chemtech article.

Meanwhile before the products of formula I', no product having the required pharmacological properties for such a utilization had been synthesized.

The method of contraception according to the invention consists of administring to the woman about 10 mg to 1 gram of the product for 1 to 5 days preferably at the end of the menstrual cycle. Preferably one takes about 25 to 200 mg of the product per day.

Preferably the product is administered orally. Administration of the product via the vagina is equally suitable.

The method of using the products of the invention to interrupt pregnancy consists in administering to warm blooded females at least a physiologically active amount of the product of formula I'.

One administers an amount on the order of about 50 mg to 1 gram per day of the product for 1 to 5 days toward the end of the menstrual cycle. Preferably 200 mg to about 500 mg is used in women.

The preferred manner of administration of this product is orally or via the vagina.

The products of formula I' can be used in synchronizing the fertile periods of animals particularly cattle and sheep. They can also be used to control the fertility of pets like dogs or cats.

Finally, the products of formula I', which have anti-androgen activity can be used for human contraception.

EXAMPLE 1

11$\beta$-(4-pyridyl)-17$\alpha$-(prop-1-ynyl-$\Delta^{4,9}$-estradiene-17$\beta$-ol-3-one

STEP A:

3,3-[1,2-ethanediyl-bisoxy]-17$\alpha$-(prop-1-ynyl)-$\Delta^{5(10),9(11)}$-estradiene-17$\beta$-ol 207 ml of a solution of 1.15% ethyl magnesium bromide in tetrahydrofuran were stirred at 0° C. while bubbling gaseous propyne dried over calcium chloride therethrough for 90 minutes and the temperature was then allowed to return to room temperature. The mixture was stirred for one hour while the bubbling was continued. Then a solution of 30 g of 3,3-[1,2-ethanediyl-bisoxy)-$\Delta^{5(10),9(11)}$-estradiene-17-one in 120 ml of anhydrous tetrahydrofuran and one drop of triethylamine was added to the mixture over 30 minutes and the mixture was stirred for 2 hours at room temperature and was then poured into a mixture of ice, distilled water and ammonium chloride. The stirred mixture was extracted 3 times with ether and the organic phase was washed with water, dried and evaporated to dryness under reduced pressure. The residue was dried under reduced pressure to obtain 35.25 g of 3,3-[1,2-ethanediyl-bisoxy]-17$\alpha$-(prop-1-ynyl)-$\Delta^{5(10),9(11)}$-estradiene-17$\beta$-ol.

NMR Spectrum (deuterochloroform):

Peaks at 0.83 ppm (hydrogens of 18-methyl); at 1.85 ppm (hydrogens of methyl of C≡C—CH$_3$); at 5.65 ppm (hydrogens of 11-carbon); at 4 ppm (hydrogens of ethylene ketal).

STEP B:

3,3-[1,2-ethanediyl-bisoxy]-5$\alpha$,10$\alpha$-epoxy-17$\alpha$-(prop-1-ynyl)-$\Delta^{9(11)}$-estrene-17$\beta$-ol.

A mixture of 30 g of the product of Step A in 150 ml of methylene chloride was stirred while bubbling nitrogen therethrough and after cooling the mixture to 0° C., 1.8 ml of hexafluoroacetone sesquihydrate were added all at once. The mixture was stirred while 4.35 ml of 85% oxygenated water were added and the mixture was stirred at 0° C. for 72 hours while continuing to bubble nitrogen therethrough. The solution was poured into a mixture of 250 g of ice and 500 ml of 0.2N sodium thiosulfate solution and the mixture was stirred for a few moments and was then extracted with methylene chloride. The organic phase was washed with distilled water, dried over sodium sulfate in the presence of pyridine and evaporated to dryness under reduced pressure. The residue was dried under reduced pressure and the 31.6 g of residue were chromatographed over silica gel. Elution with a 9-1 benzene-ethyl acetate mixture yield 3,3-[1,2-ethanediyl-bisoxy]-5$\alpha$10$\alpha$-epoxy-17$\alpha$-(prop-1-ynyl)-$\Delta^{9(11)}$-estrene-17$\beta$-ol.

NMR Spectrum (deuterochloroform): Peaks at 0.82 ppm (hydrogens of 18—CH$_3$); at 1.83 ppm (hydrogens of methyl of C≡C—CH$_3$); at 6.1 ppm (hydrogens of 11-carbon); at 3.92 ppm (hydrogens of ethylene ketal).

STEP C:

3,3-[1,2-ethanediyl-bisoxy]-11$\beta$-(4-pyridyl)-17$\alpha$-(prop-1-ynyl)-$\Delta^{9}$-estrene-5$\alpha$,17$\beta$-diol 100 ml of a tetrahydrofuran solution of 0.5 to 0.6M 4-chloropyridyl magnesium bromide prepared from 15 g of 4-chloro-pyridine and 6 g of magnesium was added at 20° C. to a solution of 6.16 g of dimethyl sulfide-cuprous bromide complex in 40 ml of tetrahydrofuran and the mixture was stirred under an inert atmosphere at room temperature for 20 minutes. Then, a solution containing 3.7 g of 3,3-[1,2-ethanediyl-bisoxy]-5$\alpha$,10$\alpha$-epoxy-17$\alpha$-(prop-1-ynyl)-$\Delta^{9(11)}$-estrene-17$\beta$-ol was added thereto over 10 minutes and the mixture was stirred at room temperature for one hour and was then poured into a mixture of cold water and ammonium chloride. The mixture was stirred at room temperature for 30 minutes and was extracted with ether. The organic phase was washed with an aqueous saturated sodium chloride solution, was dried and evaporated to dryness under reduced pressure. The 6 g of residue were chromatographed over silica gel and eluted with a 1-1 methylene chloride—acetone mixture containing 1 ppm of triethylamine to obtain 3.15 g of 3,3-[1,2-ethanediyl-bisoxy]-11$\beta$-(4-pyridyl)-17$\alpha$-(prop-1-ynyl)-$\Delta^{9}$-estrene-5$\alpha$,17$\beta$-diol which was dried towards 60° C. at 0.1 mm Hg which had a specific rotation of $[\alpha]_D^{20} = -52° \pm 1.5°$ (c=1% in chloroform).

STEP D:

11$\beta$-(4-pyridyl)-17$\alpha$-(prop-1-ynyl)-$\Delta^{4,9}$-estradiene-17$\beta$-ol-3-one A solution of 2.9 g of the product of Step C, 14 ml of methanol and 7 ml of 2N hydrochloric acid was stirred under an inert atmosphere at room temperature for 3 hours and was then admixed with a solution of 200 ml of ether and 90 ml of aqueous saturated sodium bicarbonate solution. The mixture was stirred at room temperature for 15 minutes and the decanted aqueous phase was extracted with ether. The organic phase was washed with aqueous saturated sodium chloride solution, dried and evaporated to dryness under reduced pressure. The 2.3 g of residue were chromatographed over silica gel and eluted with a 6-4 methylene chloride-acetone mixture. The 1.7 g of product was dried for 24 hours at 0.1 mm Hg and for 8 hours at 80° C. to obtain 11$\beta$-(4-pyridyl)-17$\alpha$-(prop-1-ynyl)-$\Delta^{4,9}$-estradiene-17$\beta$-ol-3-one with a specific rotation of $[\alpha]_D^{20} = +30.5° \pm 1°$ (c=1% in chloroform).

Using the same procedure, 11β-(3-pyridyl)-17α-(prop-1-ynyl)-Δ$^{4,9}$-estradiene-17β-ol-3-one with a specific rotation of $[α]_D^{20}=+14°$ (c=1% in chloroform) and 11β-(2-pyridyl)-17α-(prop-1-ynyl)-Δ$^{4,9}$-estradiene-17β-ol-3-one with a specific rotation of $[α]_D^{20}=-2°$ (c=1% in chloroform) were prepared.

EXAMPLE 2

11β-[3-(N,N-dimethylamino)-propyl]-17α-(prop-1-ynyl)-Δ$^{4,9}$-estradiene-17β-ol-3-one

STEP A:

3,3-[1,2-ethanediyl-bisoxy]-11β-[3-(N,N-dimethylamino)-propyl]-17α-(prop-1-ynyl)-Δ$^9$-estrene-5α,17β-diol 12.33 g of dimethyl sulfide-cuprous bromide complex were added over 5 minutes at 0° C. to a solution of 0.85M of 3-(N,N-dimethylamino)-propyl magnesium chloride [prepared from 42 g of chloro 3-(N,N-dimethylamino)-propane and 10.5 g of magnesium] and the mixture was stirred at 0° C. for 25 minutes. A solution of 3.70 g of 3,3-[1,2-ethanediyl-bisoxy]-5α,10α-epoxy-17α-(prop-1-ynyl)-Δ$^{9(11)}$-estrene-17β-ol in 50 ml of tetrahydrofuran was added to the mixture dropwise and the mixture was then stirred at 0° C. for 3 hours and was poured into a mixture of 40 g of ammonium chloride and 200 ml of iced water. The mixture was stirred at room temperature for 15 minutes and was then extracted with ether. The organic phase was washed with aqueous saturated sodium chloride solution, dried and evaporated to dryness under reduced pressure. The 4.6 g of residue were chromatographed over silica gel and eluted with an 8-2 methylene chloride-methanol mixture to obtain 2.55 g of 3,3-[1,2-ethanediyl-bisoxy]-11β-[3-(N,N-dimethylamino)-propyl]-17α-(prop-1-ynyl)-Δ$^9$-estrene-5α,17β-diol with a specific rotation of $[α]_D^{20}=-86°±1.5°$ (c=1% in chloroform).

STEP B:

11β-[3-(N,N-dimethylamino)-propyl]-17α-(prop-1-ynyl)-Δ$^{4,9}$-estradiene-17β-ol-3-one A mixture of 2.4 g of the product of Step A, 14 ml of methanol and 7 ml of 2N hydrochloric acid was stirred under an inert atmosphere at room temperature for 4 hours and then 200 ml of isopropyl ether and 90 ml of aqueous saturated sodium bicarbonate solution were added thereto. The mixture was stirred at room temperature for 30 minutes and the decanted aqueous phase was extracted with ether. The organic extract was washed with aqueous saturated sodium chloride solution, was dried and evaporated to dryness under reduced pressure. The 1.8 g of residue were chromatographed over silica gel and eluted with an 8-2 chloroform-methanol mixture. The 1.30 g of product were dried at 30° to 40° C. at 0.1 mm Hg to obtain 1.25 g of 11β-[3-(N,N-dimethylamino)-propyl]-17α-(prop-1-ynyl)-Δ$^{4,9}$-estradiene-17β-ol-3-one with a specific rotation of $[α]_D^{20}=-114°±2.5°$ (c=1% in chloroform).

EXAMPLE 3

11β-[4-(N,N-dimethylaminoethoxy)-phenyl]-17α-(prop-1-ynyl)-Δ$^{4,9}$-estradiene-17β-ol-3-one

STEP A:

3,3-[1,2-ethanediyl-bisoxy]-11β-[4-(N,N-dimethylaminoethoxy)-phenyl]-17α-(prop-1-ynyl)-Δ$^9$-estrene-5α,17β-diol A solution of 24 g of 4-(N,N-dimethylaminoethoxy)-bromobenzene was added dropwise over 45 minutes to 90 ml of anhydrous tetrahydrofuran and 2 ml of 1,2-dibromoethane were added as catalyst. After the addition, the mixture was stirred at 25° C. for one hour to obtain a solution of 0.7M of 4-(N,N-dimethylaminoethoxy)-bromobenzene magnesium which was then added to a solution of 6.16 g of dimethylsulfide-cuprous bromide complex in 20 ml of tetrahydrofuran. The mixture was stirred at room temperature for 20 minutes and a solution of 3.7 g of 3,3-[1,2p-(ethanediyl-bisoxy)]-5α,10α-epoxy)-17α-prop-1-ynyl-Δ$^{9(11)}$-estrene-17β-ol in 50 ml of tetrahydrofuran was added thereto dropwise over a few minutes. The mixture was stirred under an inert atmosphere for one hour and was then poured into a solution of 15 g of ammonium chloride in 20 ml of iced water. The mixture was extracted with ether and the organic phase was washed with aqueous saturated sodium chloride solution, was dried and evaporated to dryness under reduced pressure. The 18.3 g of oil were chromatographed over silica gel and eluted with chloroform to obtain 4.5 g of 3,3-[1,2-ethanediyl-bisoxy]-11β-[4-(N,N-dimethylaminoethoxy)-phenyl]-17α-(prop-1-ynyl)-Δ$^9$-estrene-5α,17β-diol with a specific rotation of $[α]_D^{20}=-44°±1.5°$ (c=1% in chloroform).

STEP B:

11β-[4-(N,N-dimethylaminoethoxy)-phenyl]-17α-(prop-1-ynyl)-Δ$^{4,9}$-estradiene-17β-ol-3-one 9.5 ml of 2N hydrochloric acid were added to a solution of 4.5 g of the product of Step A in 20 ml of methanol and the solution was stirred at room temperature for 2 hours. 260 ml of ether and 110 ml of an aqueous saturated sodium bicarbonate solution were added to the mixture which was stirred at room temperature for 15 minutes. The decanted aqueous phase was extracted with ether and the organic phase was dried and evaporated to dryness under reduced pressure. The 3.3 g of residue were chromatographed over silica gel and eluted with a 92.5-7.5 methylene chloride-methanol mixture to obtain 1.8 g of amorphous 11β-[4-(N,N-dimethylaminoethoxy)-phenyl]-17α-(prop-1-ynyl)-Δ$^{4,9}$-estradiene-17β-ol-3-one with a specific rotation of $[α]_D^{20}=+71°$ (c=1% in chloroform).

EXAMPLE 4

11β-[4,-(N,N-dimethylamino)-phenyl]-17α-(prop-1-ynyl)-Δ$^{4,9}$-estradiene-17β-ol-3-one

STEP A:

3,3-[1,2-ethanediyl-bisoxy]-11β-[4-(N,N-dimethylamino)-phenyl]-17α-(prop-1-ynyl)-Δ$^9$-estrene-5α,17β-diol A solution of 38 mmoles of p-dimethylaminophenyl magnesium bromide in tetrahydrofuran was added to a suspension of 4.1 g of a cuprous bromide-dimethylsulfide complex in 20 ml of tetrahydrofuran and then a solution of 2.45 g of 3,3-[1,2-ethanediyl-bisoxy]-5α,10α-epoxy-17α-(prop-1-ynyl)-Δ$^{9(11)}$-estrene-17β-ol in tetrahydrofuran was added thereto. The mixture was stirred for 10 minutes and was then hydrolyzed with 50 ml of aqueous saturated ammonium chloride solution. The decanted aqueous phase was extracted with ether and the organic phase was washed with water, dried and evaporated to dryness under reduced pressure. The 11 g of residue were chromatographed over silica gel and eluted with a 6-4 cyclohexane-ethyl acetate mixture of obtain 1.8 g of 3,3-[1,2-ethanediyl-bisoxy]-11β-[4-(N,N-dimethylamino)-phenyl]-17α-(prop-1-ynyl)-Δ$^9$-estrene- 5α,17β-diol which after crystallization from isopropyl ether and ethyl acetate had a specific rotoation of $[\alpha]_D^{20} = -66.5°$ (c=1% in chloroform) and a melting point of 210° C. and 750 mg of the corresponding 11α-compound.

STEP B:
11β-[4-(N,N-dimethylamino)-phenyl]-17α-(prop-1-ynyl)-Δ$^{4,9}$-estradiene-17β-ol-3-one 2 ml of concentrated hydrochloric acid were added to a solution of 1.53 g of the product of Step A in 60 ml of methanol and after stirring the mixture for 30 minutes at room temperature, 150 ml of ether and then 50 ml of aqueous N sodium hydroxide solution were added thereto. The reaction mixture was stirred for 15 minutes and the decanted organic phase was dried and evaporated to dryness under reduced pressure. The 1.4 g of residue were chromatographed over silica gel and was eluted with a 7-3 cyclohexane-ethyl acetate mixture to obtain 0.932 g of 11β-[4-(N,N-dimethylamino)-phenyl]-17α-(prop-1-ynyl)-Δ$^{4,9}$-estradiene-17β-ol-3-one melting at 150° C. and a specific rotation of $[\alpha]_D^{20} = +138.5°$ (c=0.5% in chloroform).

EXAMPLE 5
11β-[4-trimethylsilyl-phenyl]-17α-(prop-1-ynyl)-Δ$^{4,9}$-estradiene-17β-ol-3-one STEP A:
3,3-[1,2-ethanediyl-bisoxy]-11β-(4-trimethysilyl-phenyl)-17α-(prop-1-ynyl)-Δ$^9$-estrene-5α,17β-diol 200 mg of aqueous chloride were added under an inert atmosphere at −30° C. to 45 ml of solution of 0.65M of 4-trimethylsilyl-phenyl magnesium bromide in tetrahydrofuran and a solution of 3.3 g of 3,3-[1,2-ethanediyl-bisoxy]-5α,10α-epoxy-17α-(prop-1-ynyl)-Δ$^{9(11)}$-esterene-17β-ol in 25 ml of tetrahydrofuran were added thereto dropwise at −20° C. After one hour, the mixture was hydrolyzed with aqueous ammonium chloride solution and was extracted with ether. The organic phase was dried and evaporated to dryness under reduced pressure and the residue was chromatographed over silica gel. Elution with a 94-6 methylene chloride-acetone mixture containing 0.1% of triethylamine yielded 2.087 g of 3,3-[1,2-ethanediyl-bisoxy]-11β-(4-trimethylsilyl-phenyl)-17α-(prop-1-ynyl)-Δ$^9$-estrene-5α,17β-diol which after crystallization from isopropyl ether and then ethyl acetate melted at 226° C. and a specific rotation of $[\alpha]_D^{20} = -60° \pm 1.5°$ (c=0.9% in chloroform).

STEP B:
11β-(4-trimethylsilyl-phenyl)-17α-(prop-1-ynyl)-Δ$^{4,9}$-estradiene-17β-ol-3-one 1.7 g of Redex sulfonic acid resin were added to a solution of 1.68 g of the product of Step A in 17 ml of 90% alcohol and the mixture was refluxed for 30 minutes and vacuum filtered. The filter was rinsed with methylene chloride and the filtrate was evaporated to dryness under reduced pressure. The residue was taken up in methylene chloride and the solution was dried and evaporated to dryness under reduced pressure. The residue was chromatographed over silica gel and was eluted with an 85-15 benzene-ethyl acetate mixture to obtain 1.217 g of 11β-(4-trimethylsilyl-phenyl)-17α-(prop-1-ynyl)-Δ$^{4,9}$-estradiene-17β-ol-3-3-one melting at 212° C. and having a specific rotation of $[\alpha]_D^{20} = +94°$ (c=0.9% in chloroform).

The same procedure was used to prepare 11β-[3-trimethylsilyl-phenyl]-17α-(prop-1-ynyl)-Δ$^{4,9}$-estradiene-17β-ol-3-one with a specific rotation of $[\alpha]_D^{20} = +52.5° \pm 2°$ (c=1% in chloroform).

EXAMPLE 6
11β-[4-(N,N-dimethylamino)-phenyl]-17β-ethynyl-Δ$^{4,9}$-estradiene-17α-ol-3-one STEP A:
3,3-dimethoxy-17β-ethynyl-Δ$^{5(10),9(11)}$-estradiene-17α-ol A mixture of 16.8 g of 3,3-dimethoxy-17α-ethynyl-Δ$^{5(10),9(11)}$-estradiene-17β-ol, 175 ml of anhydrous tetrahydrofuran and 4.35 g of lithium bromide was stirred at room temperature for 5 minutes and then the mixture was cooled to −60° C. and 3.9 ml of methane sulfonyl chloride were added thereto. The mixture was stirred at −60° C. for one hour and was then poured into 500 ml of aqueous saturated ammonium chloride solution. The mixture was stirred for 10 minutes and was extracted with methylene chloride. The organic phase was dried and after the addition of 2.5 ml of pyridine, the mixture was evaporated to dryness at 0° C. under reduced pressure. 75 ml of tetrahydrofuran were added to the residue and 12.5 ml of 0.75 g of silver nitrate in water were added thereto. The mixture was held at −30° C. for 18 hours and at room temperature for 4 hours and was then poured into 500 ml of aqueous semisaturated ammonium chloride solution containing 5 g of sodium cyanide. The mixture was stirred at 20° C. for 30 minutes and was extracted with chloroform. The organic phase was washed with aqueous saturated sodium chloride solution, dried and evaporated to dryness under reduced pressure. The residue was chromatographed over silica gel and was eluted with a 9-1 petroleum ether-ethyl acetate mixture to obtain 3 g of 3,3-dimethoxy-17β-ethynyl-Δ$^{5(10),9(11)}$-estradiene-17α-ol melting at ∼150° C. and having a specific rotation of $[\alpha]_D^{20} = +125° \pm 2.5°$ (c=1% in chloroform).

STEP B:
3,3-dimethoxy-5α,10α-epoxy-17β-ethynyl-Δ$^{9(11)}$-estrene-17α-ol 0.12 ml of hexachloroacetone and 0.65 ml of oxygenated water (200 volumes) were added at 0° C. to a mixture of 2.6 g of the product of Step A, 12 ml of methylene chloride and one drop of pyridine and the mixture was stirred for one hour after which 13 ml of chloroform were added. The mixture was stirred for 18 hours and was then poured into 100 ml of aqueous saturated sodium thiosulfate solution. The mixture was stirred for 10 minutes and was extracted with chloroform. The organic phase was washed with aqueous saturated sodium chloride solution, dried and evaporated to dryness under reduced pressure to obtain 2.8 g of 3,3-dimethoxy-5α,10α-epoxy-17β-ethynyl-Δ$^{9(11)}$estrene-17α-ol which was used as is for the next step. The product contained a small amount of the 5β,10β-epoxy compound.

STEP C:
3,3-dimethoxy-11β-[4-(N,N-dimethylamino)-phenyl]-17β-ethynyl-Δ$^9$-estrene-5α,17α-diol A mixture of 2.8 g of the product of Step B, 56 ml of anhydrous tetrahydrofuran and 80 mg of anhydrous copper chloride was stirred under an inert atmosphere at room temperature for 5 minutes and was then placed in an ice bath. 33 ml of 0.95M 4-dimethylaminophenyl magnesium bromide in tetrahydrofuran were added dropwise to the mixture which was then allowed to return to room temperature.

63 ml of 4-dimethylaminophenyl magnesium bromide were added to a suspension of 6.15 g of dimethylsulfide-copper bromide complex in 30 ml of anhydrous tetrahydrofuran while keeping the temperature below 28.5° C. and the mixture was stirred for 30 minutes. Then, the above solution was added dropwise thereto and the mixture was stirred at room temperature for 18 hours and was then poured into aqueous saturated ammonium chloride solution. The mixture was stirred for 10 minutes and was extracted with chloroform. The organic phase was washed with water, dried and evaporated to dryness under reduced pressure. The residue was chromatographed over silica gel and was eluted with a 1-1 petroleum ether-ethyl acetate mixture containing 0.5 ppm of triethylamine. The 1.28 g of product was chromatographed over silica gel and was eluted with the same mixture to obtain 0.84 g of 3,3-dimethoxy-11$\beta$-[4-(N,N-dimethylamino)-phenyl]-17$\beta$-ethynyl-$\Delta^9$-estrene-5$\alpha$,17$\alpha$-diol.

STEP D:
11$\beta$-[4-(N,N-dimethylamino)-phenyl]-17$\beta$-ethynyl-$\Delta^{4,9}$-estradiene-17$\alpha$-ol-3-one A mixture of 0.76 g of the product of Step C, 15 ml of methanol and 1.6 ml of 2N hydrochloric acid was stirred for 90 minutes and was then poured into an aqueous saturated sodium bicarbonate solution. The mixture was extracted with chloroform and the organic phase was dried and evaporated to dryness under reduced pressure. The 0.76 g of residue was chromatographed over silica gel and was eluted with a 1-1 petroleum ether-ethyl acetate mixture and then with a 3-1 ether-petroleum ether mixture to obtain 0.435 g of 11$\beta$-[4-(N,N-dimethylamino)-phenyl]-17$\beta$-ethynyl-$\Delta^{4,9}$-estradiene-17$\alpha$-ol-3-one which after crystallization from isopropyl ether melted at 142° C. and had a specific rotation of $[\alpha]_D^{20} = +235.5° \pm 4.5°$ (c=0.45% in chloroform).

EXAMPLE 7
11$\beta$-[4-(N,N-dimethylamino)-phenyl]-17$\alpha$-phenyl-$\Delta^{4,9}$-estradiene-17$\beta$-ol-3-one

STEP A:
3,3-[1,2-ethanediyl-bisoxy]-5$\alpha$,10$\alpha$-epoxy-$\Delta^{9(11)}$-estrene-17-one 2 drops of pyridine were added to a mixture of 11.18 g of 3,3-[1,2-ethanediyl-bisoxy]-$\Delta^{5(10),9(11)}$-estradiene-17-one and 56 ml of methylene chloride and 4.3 ml of hexafluoroacetone sesquihydrate were added to the mixture at 0° C. 1.6 ml of 85% oxygenated water were added to the mixture and the mixture was stirred under an inert atmosphere at 0° C. for 23 hour and was poured into a mixture of 200 g of ice and 200 ml of 0.5M sodium thiosulfate solution. The mixture was stirred for 30 minutes and was extracted with methylene chloride containing a trace of pyridine. The organic phase was washed with water, dried and evaporated to dryness to obtain 11.4 g of 3,3-[1,2-ethanediyl-bisoxy]-5$\alpha$,10$\alpha$-epoxy-$\Delta^{9(11)}$-estrene-17-one which was used as is for the next step.

STEP B:
3,3-[1,2-ethanediyl-bisoxy]-11$\beta$-[4-(N,N-dimethylamino)-phenyl]-$\Delta^9$-estrene-5$\alpha$-ol-17-one A mixture of 200 g of 4-dimethylamino benzene bromide in 950 ml of anhydrous tetrahydrofuran was added over 2½ hours at 35° C.±50° C. to a mixture of 29 g of magnesium turnings and 50 ml of anhydrous tetrahydrofuran under an inert atmosphere to obtain a solution of 0.8M of magnesium.

284 ml of the said magnesium solution were added dropwise over 75 minutes at 0° to 5° C. under an inert atmosphere to a mixture of 25 g of the product of Step A, 500 ml of anhydrous tetrahydrofuran and 0.757 g of copper chloride and the mixture was stirred for 15 minutes and poured into aqueous saturated ammonium chloride solution. The mixture was extracted with ethyl acetate and the organic phase was washed with aqueous saturated ammonium chloride solution and with aqueous saturated sodium chloride solution, dried and evaporated to dryness under reduced pressure. The 46 g of residue were chromatographed over silica gel and were eluted with a 1-1 petroleum ether-ethyl acetate mixture containing 1 ppm of triethylamine to obtain 17.76 g of product melting at 178° C. The impure fractions were subjected again to chromatography over silica gel and were eluted with an 8-2 petroleum ether-acetone mixture containing 1 ppm of triethylamine to obtain another 6.35 g of 3,3-[1,2-ethanediyl-bisoxy]-11$\beta$-[4(N,N-dimethylamino)-phenyl]-$\Delta^9$-estrene-5$\alpha$-ol-17-one melting at 176° C. which was used as is for the next step.

STEP C:
3,3-[1,2-ethanediyl-bisoxy]-11$\beta$-[4-(N,N-dimethylamino)-phenyl]-17$\alpha$-phenyl-$\Delta^9$-estrene-5$\alpha$,17$\beta$-diol A solution of 4.51 g of the product of Step B in 45.1 ml of anhydrous tetrahydrofuran was added over 30 minutes at 25° C. to a solution of 33.3 ml of phenyllithium (1.5 moles) and the mixture was stirred for 4 hours at room temperature and was then poured into aqueous saturated ammonium chloride solution. The mixture was extracted with ether and the organic phase was washed with aqueous saturated sodium chloride solution, dried and evaporated to dryness. The 5.6 g of residue were chromatographed over silica gel and were eluted with a 9-1 methylene chloride-acetone mixture containing of triethylamine to obtain 1.16 g of 3,3-[1,2-ethanediyl-bisoxy]-11$\beta$-[4-(N,N-dimethylamino)-phenyl]-17$\alpha$-phenyl-$\Delta^9$-estrene-5$\alpha$,17$\beta$-diol which after crystallization from an isopropyl ether-methylene chloride mixture melted at 240° C. and had a specific rotation of $[\alpha]_D^{20} = +53° \pm 2.5°$ (c=0.5% in CHCl$_3$).

STEP D:
11$\beta$-[4-(N,N-dimethylamino)-phenyl]-17$\alpha$-phenyl-$\Delta^{4,9}$-estradiene-17$\beta$-ol-3-one 3 ml of 2N hydrochloric acid were added under an inert atmosphere at 0° to 5° C. to a mixture of 1.5 g of the product of Step C in 45 ml of methanol and the mixture was stirred at 0° to 5° C. for one hour. Then, 90 ml of ether and 90 ml of an aqueous 0.25M of sodium bicarbonate solution were added to the mixture and the mixture was stirred for 5 minutes. The decanted aqueous phase was extracted with ether and the organic phase was washed with aqueous saturated sodium chloride solution, dried and evaporated to dryness. The 1.3 g of residue were chromatographed over silica gel and were eluted with a 1-1 petroleum ether ether mixture to obtain 0.93 g of 11β-[4-(N,N-dimethylamino)-phenyl]-17α-phenyl-Δ$^{4,9}$-estradiene-17β-ol-3-one which after crystallization from methylene chloride-isopropyl ether melted at 226° C. and had a specific rotation of [α]$_D^{20}$= +151.5° (c=0.4% in chloroform).

EXAMPLE 8

11β-[4-(N,N-dimethylamino)-phenyl]-23-methyl-19,21-dinor-17α-Δ$^{4,9,23}$-cholatriene-20-yn-17β-ol-3-one

STEP A:
3,3-[1,2-ethanediyl-bisoxy]-11β-[4-(N,N-dimethylamino)-phenyl]-23-methyl-19,21-dinor-17α-Δ$^{9,23}$-choladiene-20-yn-5α,17β-diol 10.61 ml of 2-methyl-1-buten-3-yne were added under an inert atmosphere to a mixture of 4.5 g of potassium tert.-butylate in 90 ml of anhydrous tetrahydrofuran and the mixture was stirred for 15 minutes at −10° C. A solution of 4.5 g of the product of Step B of Example 7 in 45 ml of anhydrous tetrahydrofuran was added over 15 minutes to the reaction mixture and the mixture was stirred at −10° C. for 30 minutes and then for 4 hours at 0° to 5° C. The mixture was poured into 500 ml of aqueous saturated solution of ammonium chloride and the mixture was extracted with ethyl acetate. The organic phase was washed with aqueous saturated sodium chloride solution, dried and evaporated to dryness to obtain 5.56 g of raw 3,3-[1,2-ethanediyl-bisoxy]-11β-[4-(N,N-dimethylamino)-phenyl]-23-methyl-19,21-dinor-17α-Δ$^{9,23}$-choladiene-20-yn-5α,17β-diol melting at 205° C. which was used as is for the next step. The raw product was chromatographed over silica gel and was eluted with a 9-1 methylene chloride-ethyl acetate containing 1 part per 1000 of triethylamine and crystallized from ethyl acetate to obtain the product melting at 215° C.

STEP B:
11β-[4-(N,N-dimethylamino)-phenyl]-23-methyl-19,21-dinor-17α-Δ$^{4,9,23}$-cholatriene-20-yne-17β-ol-3-one A mixture of 5 g of the product of Step A, 300 ml of methanol and 10 ml of 2N hydrochloric acid was stirred under an inert atmosphere for 15 minutes at 20° C. and then 300 ml of methylene chloride and then 300 ml of aqueous 0.25M sodium bicarbonate solution were added thereto. The mixture was stirred for 10 minutes and the decanted aqueous phase was extracted with methylene chloride. The organic phase was washed with water, dried evaporated to dryness. The 4.5 g of residue were chromatographed over silica gel and were eluted with a 1-1 petroleum ether-ethyl acetate mixture to obtain after crystallization from diisopropyl oxide 2.01 g of 11β-[4-(N,N-dimethylamino)-phenyl]-23-methyl-19,21-dinor-17α-Δ$^{4,9,23}$-cholatriene-20-yne-17β-ol-3-one melting at 185° C. and having a specific rotation of [α]$_D^{20}$= +88.5°±1.5° (c=1% in CHCl$_3$).

EXAMPLE 9

11β-[4-(N,N-dimethylamino)-phenyl]-17β-methoxy-23-methyl-19,21-dinor-17α-Δ$^{4,9,23}$-cholatriene-20-yne-3-one 10.61 ml of 2-methyl-1-buten-3-yne were added dropwise at −10° C. to a suspension of 4.5 g of potassium tert.-butylate in 90 ml of anhydrous tetrahydrofuran under an inert atmosphere and the mixture was stirred at −10° C. for 15 minutes. Then, a mixture of 4.5 g of the product of Step B of Example 7 in 45 ml of anhydrous tetrahydrofuran was added over 15 minutes (to the mixture which was then stirred at −10° C. for 30 minutes) and at 0° to 5° C. for 4 hours. 7.5 ml of methyl iodide were added to the mixture which was then stirred in an ice bath for 30 minutes and then poured into 500 ml of 0.1N hydrochloric acid. The mixture was stirred for 30 minutes at room temperature and was then extracted with ethyl acetate. The organic phase was washed with aqueous saturated sodium bicarbonate solution, then with aqueous saturated sodium chloride solution, dried and evaporated to dryness. The residue was chromatographed over silica gel and was eluted with a 95-5 methylene chloride-ethyl acetate mixture to obtain 2.7 g of 11β-[4-(N,N-dimethylamino)-phenyl]-17β-methoxy-23-methyl-19,21-dinor-17α-Δ$^{4,9,23}$-cholatriene-20-yne-3-one which after crystallization from methanol melted at 105° C.

EXAMPLE 10

11β-[4-(N,N-dimethylamino)-phenyl]-21-chloro-19-nor-17α-Δ$^{4,9}$-pregnadiene-20-yne-17β-ol-3-one

STEP A:
3,3-[1,2-ethanediyl-bisoxy]-11β-[4-(N,N-dimethylamino)-phenyl]-21-chloro-19-nor-17α-Δ$^9$-pregnene-20-yne-5α,17β-diol A solution of 7 ml of trichloroethylene in 28 ml of anhydrous ether was added with stirring under an inert atmosphere at 0° to 5° C. to a mixture of 77.5 ml of 1M butyllithium in hexane and 310 ml of anhydrous ether and the mixture was stirred for one hour while the temperature rose to 20° C. A solution of 7 g of Step B of Example 7 in 70 ml of tetrahydrofuran was added to the resulting mixture dropwise over 30 minutes at 0° to 5° C. and the mixture was stirred at 0° to 5° C. for 30 minutes after which the temperature was allowed to rise to 20° C. and was slowly poured into an aqueous saturated ammonium chloride solution and the decanted aqueous phase was extracted with methylene chloride. The organic phase was washed with water, dried and evaporated to dryness to obtain 8.5 g of raw product melting at 220° C. The latter was added to 42.5 ml of diisopropyl oxide and the mixture was stirred for 30 minutes and vacuum filtered to obtain 6.38 g of product melting at 230° C. The latter was chromatographed over silica gel and was eluted with a 7-3 benzene-ethyl acetate mixture containing 1 ppm of triethylamine. The product was dissolved in methylene chloride and was precipitated by addition of diisopropyloxide to obtain 3,3-[1,2-ethanediyl-bisoxy]-11β-[4-(N,N-dimethylamino)-phenyl]-21-chloro-19-nor-17α-Δ$^9$-pregnene-20-yne-5α,17β-diol melting at 240° C. and having a specific rotation of [α]$_D^{20}$= −83.5°±1.5° (c=1% in CHCl$_3$).

STEP B:
11β-[4-(N,N-dimethylamino)-phenyl]-21-chloro-19-nor-17α-Δ$^{4,9}$-pregnadiene-20-yne-17β-ol-3-one 15 ml of 2N hydrochloric acid were added under an inert atmosphere to a mixture of 6.38 g of the product of Step A in 191.4 ml of 95% ethanol and after stirring the mixture for one hour, 300 ml of methylene chloride and then 200 ml of aqueous 0.25 mm sodium bicarbonate solution were added thereto. The decanted aqueous phase was extracted with methylene chloride and the organic phase was washed with water, dried and evaporated to dryness under reduced pressure. The 6 g of residue were chromatographed over silica gel and were eluted with a 7-3 benzene-ethyl acetate mixture to obtain 3.95 g of 11β-[4-(N,N-dimethylamino)-phenyl]-21- chloro-19-nor-17α-Δ⁴,⁹-pregnadiene-20-yne-17β-ol-3-one which after crystallization from ethyl acetate melted at 240° C. and had a specific rotation of $[\alpha]_D^{20} = +111° \pm 2°$ (c=1% in chloroform).

EXAMPLE 11

N-oxide of 11β-[4-(N,N-dimethylamino)-phenyl]-21-chloro-19-nor-17α-Δ⁴,⁹-pregnadiene-20-yne-17β-ol-3-one A mixture of 0.54 g of 85% M-chloroperbenzoic acid in 10.8 ml of methylene chloride was added under an inert atmosphere at 0° to 5° C. to a mixture of 1.2 g of the product of Example 10 in 24 ml of methylene chloride and the mixture was stirred for one hour at 0° to 5° C. and was then poured into aqueous 0.2N sodium thiosulfate solution. The mixture was extracted with methylene chloride and the organic phase was washed with aqueous saturated sodium bicarbonate solution, with water, dried and evaporated to dryness. The 1.3 g of residue was chromatographed over silica gel and was eluted with a 7-3 methylene chloride-methanol mixture to obtain 1.15 g of N-oxide of 11β-[4-(N,N-dimethylamino)-phenyl]-21-chloro-19-nor-17α-Δ⁴,⁹-pregnadiene-20-yne-17β-ol-3-one with a specific rotation of $[\alpha]_D^{20} = +47.5° \pm 1.5°$ (c=0.7% in chloroform).

EXAMPLE 12

N-oxide of 11β-[4-(N,N-dimethylamino)-phenyl]-9α,10α-epoxy-21-chloro-19-nor-17α-Δ⁴-pregnene-20-yne-17β-ol-3-one A mixture of 1.17 g of 85% m-chloroperbenzoic acid in 23.4 ml of methylene chloride was added over 15 minutes at 0° to 5° C. to a solution of 1.18 g of the product of Example 10 in 23.6 ml of methylene chloride and the mixture was stirred for 2 hours at 20° C. after which another 1.17 g of 85% M-chloroperbenzoic acid were added. The mixture was stirred for one hour and was poured into a solution of aqueous 0.2N sodium thiosulfate. The mixture was extracted with methylene chloride and the organic phase was washed with aqueous saturated sodium bicarbonate solution and then with water, dried and evaporated to dryness to obtain 1.14 g of residue melting at 220° C. The residue was chromatographed over silica gel and was eluted with an 8-2 methylene chloride-methanol mixture to obtain 1 g of N-oxide of 11β-[4-(N,N-dimethylamino)-phenyl]-9α,10α-epoxy-21-chloro-19-nor-17α-Δ⁴-pregnene-20-yne-17β-ol-3-one melting at 270° C. and having a specific rotation of $[\alpha]_D^{20} = +39.5° \pm 2.5°$ (c=0.5% in chloroform).

EXAMPLE 13

9α,10α-epoxy-11β-[4-(N,N-dimethylamino)-phenyl]-21-chloro-19-nor-17α-Δ⁴-pregnene-20-yne-17β-ol-3-one 0.34 g of triphenylphosphine were added under an inert atmosphere to a mixture of 0.63 g of the product of Example 12 in 6.3 ml of acetic acid and the mixture was stirred at room temperature for 45 minutes and was then poured into water. The mixture was extracted with methylene chloride and the organic phase was washed with water, dried and evaporated to dryness. The 0.9 g of residue was chromatographed over silica gel and was eluted with a 1-1 petroleum ether-ethyl acetate mixture. The product was crystallized from a methylene chloride-isopropyl ether mixture to obtain 0.346 g of 9α,10α-epoxy-11α-[4-(N,N-dimethylamino)-phenyl]-21-chloro-19-nor-17α-Δ⁴-pregnene-20-yne-17β-ol-3-one melting at 265° C. and having a specific rotation of $[\alpha]_D^{20} = +45° \pm 2°$ (c=0.8% in chloroform).

EXAMPLE 14

11β-[4-(N,N-dimethylamino)-phenyl]-21-phenyl-19-nor-17α-Δ⁴,⁹-pregnadiene-20-yne-17β-ol-3-one

STEP A:

3,3-[1,2-ethanediyl-bisoxy]-11β-[4-(N,N-dimethylamino)-phenyl]-21-phenyl-19-nor-17α-Δ⁹-pregnene-20-yne-5α,17β-diol A mixture of 4.17 g of potassium tert.-butylate in 83 ml of anhydrous tetrahydrofuran was stirred under an inert atmosphere for 10 minutes and then 4.5 ml of phenyl acetylene were added dropwise at −10° C. The suspension was stirred for 5 minutes and then a solution of 4.17 g of the product of Step B of Example 7 in 41 ml of anhydrous tetrahydrofuran was added thereto dropwise at −10° C. Then, the temperature rose to 0° C. and held there for one hour and was then poured into an aqueous saturated ammonium chloride solution. The mixture was extracted with ether and the organic phase was washed with aqueous saturated sodium chloride solution, dried and evaporated to dryness. The 4.7 g of residue were chromatographed over silica gel and eluted with a 95-5 methylene chloride-acetone mixture to obtain 3.71 of of 3,3-[1,2-ethanediyl-bisoxy]-11β-[4,(N,N-dimethylamino-phenyl]-21-phenyl-19-nor-17α-Δ⁹-pregnene-20-yne-5α,17β-diol melting at 168° C. and having a specific rotation of $[\alpha]_D^{20} = -119.5° \pm 2°$ (c=1% in chloroform).

STEP B:

11β-[4-(N,N-dimethylamino)-phenyl]-21-phenyl-19-nor-17α-Δ⁴,⁹-pregnadiene-20-yne-17β-ol-3-one 6.3 ml of 2N hydrochloric acid were added to a solution of 3.49 g of the product of Step A in 68 ml of methanol and the mixture was stirred for 30 minutes and was poured into a mixture of 180 ml of ether and 90 ml of aqueous 0.25M sodium bicarbonate solution. The mixture was stirred for 5 minutes and the decanted aqueous phase was extracted with ether. The organic phase was washed with aqueous 0.25M sodium bicarbonate solution, then with aqueous sodium chloride, dried and evaporated to dryness. The 4.35 g of residue were chromatographed over silica gel and eluted with with a 95-5 methylene chloride-acetone mixture to obtain 2.13 g of 11β-[4-(N,N-dimethylamino)-phenyl]-21-phenyl-19-nor-17α-Δ⁴,⁹-pregnadiene-20-yne-17β-ol-3-one which after crystallization from isopropyl ether had a specific rotation of $[\alpha]_D^{20} = +22.5° \pm 1°$ (c=1% in chloroform).

EXAMPLE 15

11β-[4-(N,N-dimethylamino)-phenyl]-17α-(propa-1,2-dienyl)-Δ⁴,⁹-estradiene-17β-ol-3-one

STEP A:

3,3-[1,2-ethanediyl-bisoxy]-11β-[4-(N,N-dimethylamino)-phenyl]-17α-(propa-1,2L-dienyl)-Δ⁹-estrene-5α,17β-diol and
3,3-[1,2-ethanediyl-bisoxy]-11β-[4-(N,N-dimethylamino)-phenyl]-17α-(prop-2-ynyl)-Δ⁹-estrene-5α,17β-diol Allene was bubbled into 50 ml of anhydrous tetrahydrofuran at 0° to 5° C. until 2,1 g were absorbed and 23.9 ml of a solution of a 1.3M of butyllithium in hexane were added thereto over 15 minutes at −70° C. The mixture was stirred at −70° C. for 15 minutes and then a solution of 3.5 g of the product of Step B of Example 7 in 35 ml of anhydrous tetrahydrofuran were added thereto at −70° C. over 25 minutes. The mixture was stirred at −70° C. for one hour and was poured slowly into an iced aqueous saturated ammonium chloride solution. The mixture was extracted with ether and the organic phase was washed with aqueous saturated sodium chloride solution, dried and evaporated to dryness. The 3.4 g of residue were chromatographed over silica gel and eluted with a 1-1 petroleum ether-ethyl acetate mixture containing 1 ppm of triethylamine to obtain 1.73 g of 3,3-[1,2-ethanediyl-bisoxy]-11β-[4-(N,N-dimethylamino)-phenyl]-17α-(propa-1,2-dienyl)-Δ$^9$-estrene-5α,17β-diol melting at 178° C. and having a specific rotation of $[\alpha]_D^{20} = -32° \pm 2°$ (c=0.7% in chloroform) and 1.5 g of 3,3-[1,2-ethanediyl-bisoxy]-11β-[4-(N,N-dimethylamino)-phenyl]-17α-(prop-2-ynyl)-Δ$^9$-estrene-5α,17β-diol melting at 150° C. and having a specific rotation of $[\alpha]_D^{20} = -15° \pm 2°$ (c=0.9% in chloroform).

STEP B:

11β-[4-(N,N-dimethylamino)-phenyl]-17α-(propa-1,2-dienyl)-Δ$^{4,9}$-estradiene-17β-ol-3-one A mixture of 1.73 g of the 17α-(propa-1,2-dienyl)isomer of Step A, 51.8 ml of 95% ethanol and 3.5 ml of 2N hydrochloric acid was stirred under an inert atmosphere at 20° C. for one hour and then 50 ml of methylene chloride and 50 ml of aqueous 0.25M sodium bicarbonate solution were added thereto. The decanted aqueous phase was extracted with methylene chloride and the organic phase was washed with water, dried and evaporated to dryness. The 1.51 g of residue were dissolved in 10 ml of hot methylene chloride and 15 ml of isopropyl ether were added to the solution. The mixture was concentrated and allowed to stand to obtain 1.23 g of product which were crystallized form a methylene chloride-isopropyl ether mixture to obtain 1.11 g of 11β-[4-(N,N-dimethylamino)-phenyl]-17α-(propa-1,2-dienyl)-Δ$^{4,9}$-estradiene 17β-ol-3-one melting at 228° C. and having a specific rotation of $[\alpha]_D^{20} = +139.5° \pm 3°$ (c=0.8% in chloroform).

EXAMPLE 16

11β-[4-(N,N-dimethylamino)-phenyl]-17α-(prop-2-ynyl)-Δ$^{4,9}$-estradiene-17β-ol-3-one A mixture of 0.94 g of the 17α-(prop-2-ynyl)-isomer of Step A of Example 15, 28.2 ml of 95% ethanol and 2 ml of 2N hydrochloric acid was stirred at 20° C. for one hour and then 50 ml of methylene chloride and 50 ml of an aqueous 0.25M sodium bicarbonate solution were added thereto. The mixture was stirred for 5 minutes and the decanted aqueous phase was extracted with methylene chloride. The organic phase was washed with water, dried and evaporated to dryness and the residue was chromatographed over silica gel. Elution with a 1-1 petroleum ether-ethyl acetate mixture yielded 0.42 g of 11β-[4-(N,N-dimethylamino)-phenyl]-17α-(prop-2-ynyl)-Δ$^{4,9}$-estradiene-17β-ol-3-one with a specific rotation of $[\alpha]_D^{20} = +143° \pm 3°$ (c=0.8% in chloroform).

EXAMPLE 17

11β-[4-(N,N-dimethylamino)-phenyl]-17α-ethynyl-Δ$^{4,9}$-estradiene 17β-ol-3-one

STEP A:

3,3-[1,2-ethanediyl-bisoxy]-11β-[4-(N,N-dimethylamino)-phenyl]-17β-cyano-17α-trimethylsilyloxy-Δ$^9$-estrene-5α-ol A solution of 18 mmoles of [4-(N,N-dimethylamino)-phenyl]-magnesium bromide in anhydrous tetrahydrofuran was added under an inert atmosphere to a suspension of 2.05 g of dimethylsulfide-copper bromide complex in 10 ml of anhydrous tetrahydrofuran and the mixture was stirred for 30 minutes after which 20 ml of anhydrous triethylamine were added thereto. A solution of 0.95 g of 3,3-[1,2-ethanediyl-bisoxy]-5α,10α-epoxy-17β-cyano-17α-trimethylsilyloxy-Δ$^{9(11)}$-estrene in anhydrous tetrahydrofuran were added to the mixture which was then stirred for 15 hours at room temperature and poured into 50 ml of aqueous saturated ammonium chloride solution. The decanted aqueous phase was extracted with ether and the organic phase was washed with water, dried and evaporated to dryness. The residue was chromatographed over silica gel and was eluted with an 8-2 benzene-ethyl acetate mixture to obtain 1.1 g of 3,3-[1,2-ethanediyl-bisoxy]-11β-[4-(N,N-dimethylamino)-phenyl]-17β-cyano-17α-trimethylsilyloxy-Δ$^9$-estrene-5α-ol which after crystallization from isopropyl ether melted at 247° C. and had a specific rotation of $[\alpha]_D^{20} = -12.5°$ (c=1% in chloroform).

STEP B:

3,3-[1,2-ethanediyl-bisoxy]-11β-[4-(N,N-dimethylamino)-phenyl]-17α-ethynyl-Δ$^9$-estrene-5α,17β-diol 1 g of the acetylide complex of lithium ethylene-diamine was added to a mixture of 0.8 g of the product of Step A in 8 ml of ethylenediamine and the mixture was stirred under an inert atmosphere at ∼50° C. for 90 minutes. The mixture was cooled to 20° C. and was poured into aqueous ammonium chloride solution. The mixture was extracted with ether and methylene chloride and the organic phase was dried and evaporated to dryness. The residue was chromatographed over silica gel and was eluted with a 7-3 benzene-ethyl acetate mixture. The product was crystallized from isopropyl ether to obtain 0.43 g of 3,3-[1,2-ethanediyl-bisoxy]-11β-[4-(N,N-dimethylamino)-phenyl]-17α-ethynyl-Δ$^9$-estrene-5α,17β-diol melting at 199° C. and having a specific rotation of $[\alpha]_D^{20} = -43° \pm 1.5°$ (c=1% in chloroform).

STEP C:

11β-[4-(N,N-dimethylamino)-phenyl]-17α-ethynyl-Δ$^{4,9}$-estradiene-17β-ol-3-one 1 ml of 2N hydrochloric acid was added to a solution of 0.25 g of the product of Step B in 6 ml of methanol and the mixture was stirred at 20° C. for 40 minutes and then was poured into water containing 2.5 ml of N sodium hydroxide. The mixture was extracted with ether and the organic phase was dried and evaporated to dryness. The residue was chromatographed over silica gel and was eluted with a 7-3 benzene-ethyl acetate mixture to obtain 0.25 of 11β-[4-(N,N-dimethylamino)-phenyl]-17α-ethynyl-Δ$^{4,9}$-estradiene-17β-ol-3-one.

Analysis: $C_{28}H_{33}NO_2$; molecular weight=415.54 Calculated: %C 80.92; %H 8.00; %N 3.37; Found: %O 80.7 %H 8.1; %N 3.1.

EXAMPLE 18

11β-[4-(N,N-dimethylamino)-phenyl]-17α-ethynyl-Δ$^{4,9}$-estradiene-17β-ol-3-one

STEP A:

3,3-[1,2-ethanediyl-bisoxy]-11β-[4-(N,N-dimethylamino)-phenyl]-17α-ethynyl-Δ$^9$-estrene-5α,17β-diol 12.25 g of the acetylide complex of lithium ethylenediamine were added under an inert atmosphere to a solution of 6 g of the product of Step B of Example 7 in 180 ml of tetrahydrofuran and the mixture was stirred at 55° C. for 4 hours and was then cooled and poured into 600 ml of an iced aqueous saturated ammonium chloride solution. The mixture was extracted with ether and the organic phase was washed with aqueous saturated sodium chloride solution, dried and evaporated to dryness. The residue was chromatographed over silica gel and eluted with a 7-3 benzene-ethyl acetate mixture containing 1 ppm of triethylamine. The 4.5 g of product was crystallized from a methylene chloride-diisopropyl oxide mixture to obtain 3,3-[1,2-ethanediyl-bisoxy]-11β-[4-(N,N-dimethylamino)-phenyl]-17α-ethynyl-Δ$^9$-estrene-5α,17β-diol melting at 202° C. and having a specific rotation of $[\alpha]_D^{20}=47.5°\pm1.5°$ (c=1% in chloroform).

STEP B:

11β-[4-(N,N-dimethylamino)-phenyl]-17α-ethynyl-Δ$^{4,9}$-estradiene-17β-ol-3-one 5 ml of 2N hydrochloric acid were added to a suspension of 2 g of the product of Step A in 50 ml of 95% ethanol and the mixture was stirred at 20° C. for one hour. 100 ml of ether and then 100 ml of aqueous. 0.25M sodium bicarbonate solution were added to the mixture and the decanted aqueous phase was extracted with ether. The organic phase was washed with aqueous saturated sodium chloride solution, dried and evaporated to dryness and the residue was chromatographed over silica gel. Elution with a 6-4 petroleum ether-ethyl acetate mixture yielded 1.52 g of 11β-[4-(N,N-dimethylamino)-phenyl]-17α-ethynyl-Δ$^{4,9}$-estradiene-17β-ol-3-one which after crystallization from diisopropyl oxide melted at 172° C. and had a specific rotation of $[\alpha]_D^{20}=+182°\pm2.5°$ (c=1% in chloroform).

EXAMPLE 19

11β-[3-(N,N-dimethylamino)-phenyl]-17α-(prop-1-ynyl)-Δ$^{4,9}$-estradiene-17β-ol-3-one

STEP A:

3,3-[1,2-ethanediyl-bisoxy]-11β-[3-(N,N-dimethylamino)-phenyl]-17α-(prop-1-ynyl)-Δ$^9$-estrene-5α,17β-dio A mixture of 10 g of m-bromo-dimethylaniline in 45 ml of anhydrous tetrahydrofuran was added under an inert atmosphere over 45 minutes to a mixture of 1.46 g of magnesium and 5 ml of anhydrous tetrahydrofuran and the reaction was started by addition of dibromomethane. The mixture was stirred for one hour to obtain a solution of 0.95M of magnesium and 42.2 ml of the solution were added at 0° to 5° C. over 30 minutes under an inert atmosphere to a mixture of 3.7 g of 3,3-[1,2-ethanediyl-bisoxy]-5α,10α-epoxy-17α-(prop-1-ynyl)-Δ$^{9(11)}$-estrene-17β-ol, 74 ml of anhydrous tetrahydrofuran and 99 mg of copper chloride and the mixture was stirred for 30 minutes at 0° to 5° C. and was poured into an aqueous saturated ammonium chloride solution. The mixture was extracted with ether and the organic phase was washed with aqueous saturated sodium chloride solution, dried and evaporated to dryness. The residue was chromatographed over silica gel and eluted with a 9-1 methylene chloride-acetone mixture containing 1 part per 1000 triethylamine to obtain 3.5 g of 3,3-[1,2-ethanediyl-bisoxy]-11β-[3-(N,N-dimethylamino)-phenyl]-17α-(prop-1-ynyl)-Δ$^9$-estrene-5α,17β-diol melting at 262° C. and having a specific rotation of $[\alpha]_D^{20}=-64°\pm1.5°$ (c=1% in chloroform) and 0.66 g of the corresponding 5β-ol isomer melting at 210° C. and having a specific rotation of $[\alpha]_D^{20}=+32.5°\pm1°$ (c=0.8% in chloroform).

STEP B:

11β-[3-(N,N-dimethylamino)-phenyl]-17α-(prop-1-ynyl)-Δ$^{4,9}$-estradiene-17β-ol-3-one 10 ml of 2N hydrochloric acid were added at 0° to 5° C. under an inert gas to a mixture of 3.3 g of the product of step A in 100 ml of methanol and the mixture was stirred at 0° to 5° C. for one hour. 200 ml of diethyl oxide and then 200 ml of aqueous 0.25M sodium bicarbonate solution were added to the mixture which was then stirred for 5 minutes. The decanted aqueous phase was extracted with diethyloxide and the organic phase was washed with aqueous saturated sodium chloride solution, dried and evaporated to dryness. The 3 g of residue were chromatographed over silica gel and eluted with a 7-3 benzene-ethyl acetate mixture to obtain 1.43 g of amphorous 11β-[3-(N,N-dimethylamino)-phenyl]-17α-(prop-1-ynyl)-Δ$^{4,9}$-estradiene-17β-ol-3-one with a specific rotation of $[\alpha]_D^{20}=+43°\pm2.5°$ (c=1% in CHCl$_3$).

EXAMPLE 20

N-oxide of 11β-[4-(N,N-dimethylamino)-phenyl]-17α-(prop-1-ynyl)-Δ$^{4,9}$-estradiene-17β-ol-3-one A solution of 0.71 g of 85% m-chloroperbenzoic acid in 14.2 ml of methylene chloride was added over 10 minutes at 0° to 5° C. to a mixture of 1.5 g of the product of Example 4 in 30 ml of methylene chloride and the mixture was stirred for one hour at 0° to 5° C. and was poured into 100 ml of an aqueous 0.2N sodium thiosulfate solution. The decanted aqueous phase was extracted with methylene chloride and the organic phase was washed with aqueous 0.5M sodium bicarbonate solution, dried and evaporated to dryness. The residue was dissolved in 20 ml of methylene chloride and 20 ml of diisopropyl oxide were added thereto. Crystallization was induced and the mixture stood for a while and was vacuum filtered. The crystals were dried to obtain 1.4 g of N-oxide of 11β-[4-(N,N-dimethylamino)-phenyl]-17α-(prop-1-ynyl)-Δ$^{4,9}$-estradiene-17β-ol-3-one melting at 210° C. and having a specific rotation of $[\alpha]_D^{20}=+73.5°\pm2°$ (c=1% in chloroform).

EXAMPLE 21

11β-[4-(N,N-dimethylamino)-phenyl]-Δ$^{4,9}$-estradiene-17β-ol-3-one 106 mg of sodium borohydride were added to a solution of 1 g of the product of Step B of Example 7 in 20 ml of tetrahydrofuran containing 10% water and the mixture was stirred for one hour and poured into 200 ml of water. The mixture was extracted with methylene chloride and the organic phase was washed with aqueous saturated sodium chloride solution, dried and evaporated to dryness to obtain 1.3 g of 11β-[4-(N,N-dimethylamino)-phenyl]-Δ$^{4,9}$-estradiene-5α,17β-diol-3-one. 0.63 g of the latter were added to a mixture of 12 ml of methanol and 2.4 ml of 2N hydrochloric acid and the mixture was stirred at room temperature for 90 minutes and was poured into aqueous sodium bicarbonate. The mixture was extracted with ether and the organic phase was washed with aqueous saturated sodium chloride solution, dried and evaporated to dryness. The residue was chromatographed over silica gel and was eluted with a 6-4 petroleum ether-ethyl acetate mixture. The residue was triturated with petroleum ether and vacuum filtered to obtain 0.38 g of 11β-[4-(N,N-dimethylamino)-phenyl]-Δ$^{4,9}$-estradiene-17β-ol-3-one melting at 130° C. and having a specific rotation of $[\alpha]_D^{20} = +277° \pm 5°$ (c=0.5% in chloroform).

EXAMPLE 22

11β-[4-(N,N-dimethylamino)-phenyl]-17α-(prop-2-enyl)-Δ$^{4,9}$-estradien-17β-ol-3-one

STEP A:
3,3-[1,2-ethanediyl-bisoxy]-11β-[4-(N,N-dimethylamino)-phenyl]-17α-(prop-2-enyl)-Δ$^9$-estrene-5α,17β-diol A solution of 3.5 g of the product of Step B of Example 7 in 35 ml of tetrahydrofuran was added under an inert atmosphere at 20° C. over 15 minutes to 55.5 ml of 0.7M allyl magnesium bromide in ether and the mixture was stirred at 20° C. for one hour and was then poured into an aqueous saturated ammonium chloride solution. The mixture was extracted with ether and the organic phase was washed with aqueous saturated sodium chloride solution, dried and evaporated to dryness. The residue was dissolved in 10 ml of methylene chloride and 15 ml of diisopropyl oxide were added to the solution which was then concentrated and allowed to stand. The mixture was vacuum filtered and the crystals were rinsed with diisopropyl oxide and dried to obtain 2.76 g of 3,3-[1,2-ethanediyl-bisoxy]-11β-[4-(N,N-dimethylamino)-phenyl]-17α-(prop-2-enyl)-Δ$^9$-estrene-5α,17β-diol melting at 198° C.

Analysis: $C_{31}H_{43}NO_4$; molecular weight=493.69 Calculated: %C 74.42; %H 8.78; %N 2.83; Found: %C 74.0 %H 8.7; %N 2.9.

STEP B:
11β-[4-(N,N-dimethylamino)-phenyl]-17α-(prop-2-enyl)-Δ$^{4,9}$-estradiene-17β-ol-3-one 4.5 ml of 2N hydrochloric acid were added to a suspension of 2.2 g of the product of Step A in 66 ml of methanol and the mixture was stirred at 20° C. for 30 minutes after which 132 ml of diethyl oxide and then 132 ml of aqueous 0.25M sodium bicarbonate solution were added thereto. The decanted aqueous phase was extracted with diethyl oxide and the organic phase was washed with aqueous saturated sodium chloride solution, dried and evaporated to dryness. The residue was chromatographed over silica gel and was eluted with a 7-3 benzene-ethyl acetate mixture. The product was taken up in a mixture of 15 ml of diisopropyl oxide and 7.5 ml of methylene chloride and the solution was concentrated and allowed to stand. The mixture was vacuum filtered and the crystals were rinsed with diisopropyl oxide and dried to obtain 1.365 g of 11β-[4-(N,N-dimethylamino)-phenyl]-17α-(prop-2-enyl)-Δ$^{4,9}$-estradiene-17β-ol-3-one melting at 182° C. and having a specific roation of $[\alpha]_D^{20} = +206.5° \pm 3°$ (c=1% in chloroform).

EXAMPLE 23

11β-[4-(N,N-dimethylaminomethyl)-phenyl]-17α-(prop-1-ynyl)-Δ$^{4,9}$-estradiene-17β-ol-3-one

STEP A:
3,3-[1,2-ethanediyl-bisoxy]-11β-[4-(N,N-dimethylaminomethyl)-phenyl]-17α-(prop-1-ynyl)-Δ$^9$-estrene-5α,17β-diol A solution of 42.8 g of 4-(N,N-dimethylaminomethyl)bromobenzene in 190 ml of anhydrous tetrahydrofuran was added over 90 minutes under an inert atmosphere at 45° to 50° C. to a mixture of 5.5 g of magnesium in 10 ml of anhydrous tetrahydrofuran and the reaction was induced with dibromoethane addition. The mixture was stirred for one hour to obtain an 0.85M magnesium solution and 127 ml of the said solution were added under an inert atmosphere at 0° to 5° C. over one hour to a mixture of 10 g of 3,3-[1,2-ethanediyl-bisoxy]-5α,10α-epoxy-17α-(prop-1-ynyl)-Δ$^{9(11)}$-estrene-17β-ol, 200 ml of anhydrous tetrahydrofuran and 0.27 g of copper chloride. The mixture was stirred for 15 minutes and was poured into an aqueous saturated ammonium chloride solution. The mixture was extracted with ether and the organic phase was washed with aqueous saturated sodium chloride solution, dried and evaporated to dryness. The residue was chromatographed over silica gel and was eluted with a 9-1 methylene chloride-methanol mixture containing 1 part per 1000 p of triethylamine to obtain 10.1 g of product. The latter was dissolved in methylene chloride and a few drops of methanol and then diisopropyl oxide were added thereto. The mixture was concentrated, allowed to stand for 6 hours and was vacuum filtered to obtain 7.37 g of 3,3-[1,2-ethanediyl-bisoxy]-11β-[4-(N,N-dimethylaminomethyl)-phenyl]-17α-(prop-1-ynyl)-Δ$^9$-estrene-5α,17β-diol melting at 186° C. and having a specific rotation of $[\alpha]_D^{20} = -63° \pm 2.5°$ (c=0.5% in chloroform).

STEP B:
11β-[4-(N,N-dimethylaminomethyl)-phenyl]-17α-(prop-1-ynyl)-Δ$^{4,9}$-estradiene-17β-ol-3-one A mixture of 15 ml of 2N hydrochloric acid, 7.37 g of the product of Step A and 147.4 ml of methanol was stirred at 20° C. for one hour and then 300 ml of diethyl oxide and 300 ml of aqueous 0.25M sodium bicarbonate solution were added thereto. The decanted aqueous phase was extracted with diethyl oxide and the organic phase was washed with aqueous saturated sodium chloride solution, dried and evaporated to dryness. The product was dissolved in a mixture of diisopropyl oxide and methylene chloride and the solution was concentrated and allowed to stand. The mixture was vacuum filtered and the crystals were dried to obtain 3.74 g of 11β-[4-(N,N-dimethylaminomethyl)-phenyl]-17α-(prop-1-ynyl)-Δ$^{4,9}$-estradiene-17β-ol-3-one melting at 190° C. and having a specific rotation of $[\alpha]_D^{20} = +84.5° \pm 2°$ (c=0.8% in chloroform).

EXAMPLE 24

11β-(4-pyrrolidinyl-phenyl)-17α-(prop-1-ynyl)-Δ[4,9]-estradiene-17β-ol-3-one

STEP A:
3,3-[1,2-ethanediyl-bisoxy]-11β-(4-pyrrolidinylphenyl)-17α-(prop-1-ynyl)-Δ[9]-estrene-5α,17β-diol A solution of 34 g of 4-pyrrolidinyl-bromobenzene in 140 ml of anhydrous tetrahydrofuran was added over one hour under an inert atmosphere at 45°–50° C. to a mixture of 4 g of magnesium and 10 ml of anhydrous tetrahydrofuran and the reaction was started by addition of dibromoethane to obtain a 1M magnesium solution. 86.4 ml of the said solution were added over 90 minutes at 0° to 5° C. under an inert atmosphere to a mixture of 8 g of 3,3-[1,2-ethanediyl-bisoxy]-5α,10α-epoxy-17α-(prop-1-ynyl)-Δ[9(11)]-estrene-17β-ol in 160 ml of anhydrous tetrahydrofuran and 216 mg of copper chloride and the mixture was stirred for one hour and was poured into an aqueous saturated ammonium chloride solution. The mixture was extracted with diethyl oxide and the organic phase was washed with aqueous saturated ammonium chloride solution, aqueous saturated sodium chloride solution, dried and evaporated to dryness. The residue was chromatographed over silica gel and was eluted with a 95-5 methylene chloride-acetone mixture containing part per 1000 of triethylamine to obtain 8.3 g of 3,3-[1,2-ethanediyl-bisoxy]-11β-(4-pyrrolidinyl-phenyl)-17α-(prop-1-ynyl)-Δ[9]-estrene-5α,17β-diol which after crystallization from a methylene chloride-isopropyl ether mixture melted at 185° C. and had a specific rotation of $[\alpha]_D^{20} = -67° \pm 1.5°$ (c=1% in chloroform).

STEP B:
11β-(4-pyrrolidinyl-phenyl)-17α-(prop-1-ynyl)-Δ[4,9]-estradiene-17β-ol-3-one A mixture of 13 ml of 2N hydrochloric acid, 6.4 g of the product of Step A and 128 ml of methanol was stirred at 20° C. for one hour and then 256 ml of diethyl oxide and 256 ml of aqueous 0.25M sodium bicarbondate solution were added thereto. The decanted aqueous phase was extracted with diethyl oxide and the organic phase was washed with aqueous 0.25M sodium bicarbonate solution, with aqueous saturated sodium chloride solution, dried and evaporated to dryness. The residue was chromatographed over silica gel and was eluted with a 1-1 petroleum ether-ethyl acetate mixture to obtain 5.25 g of 11β-(4-pyrrolidinyl-phenyl)-17α-(prop-1-ynyl)-Δ[4,9]-estradiene-17β-ol-3-one which after crystallization from a methylene chloride-diisopropyl oxide mixture melted at 190° C. and had a specific rotation of $[\alpha]_D^{20} = +120° \pm 2.5°$ (c=1.2% in chloroform).

EXAMPLE 25

11β-[4-(N,N-dimethylamino)-phenyl]-17α-ethenyl-Δ[4,9]-estradiene-17β-ol-3-one

STEP A:
3,3-[1,2-ethanediyl-bisoxy]-11β-[4-(N,N-dimethylamino)-phenyl]-17α-ethenyl-Δ[9]-estrene-5α,17β-diol A current of hydrogen was passed for one hour through a mixture of 3 g of the product of Step B of Example 17, 60 ml of anhydrous pyridine and 0.6 g of 5% palladized calcium carbonate at room temperature and the mixture was then vacuum filtered. The filtrate was evaporated to dryness and the residue was taken up in toluene. The solution was evaporated to dryness to obtain 2.94 g of 3,3-[1,2-ethanediyl-bisoxy]-11β-[4-(N,N-dimethylamino)-phenyl]-17α-ethenyl-Δ[9]-estrene-5α,17β-diol melting at 181° C. which was used as is for the next step. A sample after crystallization from a mixture of methylene chloride-diisopropyl oxide melted at 182° C. and had a specific rotation of $[\alpha]_D^{20} = -6.5° \pm 2°$ (c=0.7% in chloroform).

STEP B:
11β-[4-(N,N-dimethylamino)-phenyl]-17α-ethenyl-Δ[4,9]-estradiene-17β-ol-3-one A mixture of 6.2 ml of 2N hydrochloric acid, 2.94 g of the product of Step A and 60 ml of methanol was stirred at 20° C. for one hour and then 120 ml of ether and 120 ml of aqueous 0.25M sodium bicarbonate solution were added thereto. The mixture was stirred for 10 minutes and the decanted aqueous phase was extracted with ether. The organic phase was washed with aqueous 0.25M sodium bicarbonate solution, aqueous saturated sodium chloride solution, dried and evaporated to dryness. The 2.65 g of residue were chromatographed over silica gel and eluted with a 7-3 benzene-ethyl acetate mixture. The product was crystallized from a diisopropyl oxide-methylene chloride mixture to obtain 1.51 g of 11β-[4-(N,N-dimethylamino)-phenyl]-17α-ethenyl-Δ[4,9]-estradiene-17β-ol-3-one melting at 150° C. and having a specific rotation of $[\alpha]_D^{20} = +243° \pm 3°$ (c=0.8% in chloroform).

EXAMPLE 26

11β-[4-(N,N-diethylamino)-phenyl]-17α-(prop-1-ynyl)-Δ[4,9]-estradiene-17β-ol-3-one

STEP A: 4-(N,N-diethylamino)-bromobenzene 93 g of bromine were added dropwise to a solution of 86 g of N,N-diethylaniline in 400 ml of acetic acid and the mixture was poured into an ice-water mixture. The mixture was extracted with methylene chloride and the organic phase was washed with aqueous sodium bicarbonate solution, dried and evaporated to dryness to obtain 125 g of 4-(N,N-diethylamino)-bromobenzene boiling at 97° C. at 0.6 mm Hg.

STEP B:
3,3-[1,2-ethanediyl-bisoxy]-11β-[4-(N,N-diethylamino)-phenyl]-17α-(prop-1-ynyl)-Δ[9]-estrene-5α,17β-diol A solution of 34.2 g of 4-(N,N-diethylamino)-bromobenzene in 110 ml of tetrahydrofuran was added at 35° C. under an inert atmosphere to a mixture of 3.9 g of magnesium and 10 ml of tetrahydrofuran to obtain a 1M magnesium solution and 80 ml of the said solution was slowly added with stirring at 0° to 5° C. under an inert atmosphere to a solution of 7.4 g of 3,3-[1,2-ethanediyl-bisoxy]-5α,10α-epoxy-17α-(prop-1-ynyl)-Δ[9(11)]-estrene-17β-ol, 150 ml of anhydrous tetrahydrofuran and 0.25 g of copper chloride. The mixture was stirred at 20° C. for 17 hours and was then poured into an aqueous ammonium chloride solution. The mixture was extracted with ether and the organic phase was washed with aqueous sodium bicarbonate solution, dried and evaporated to dryness. The residue was empasted with petroleum ether and treated with activated carbon in ether. The product was crystallized from isopropyl ether to obtain 4 g of 3,3-[1,2-ethanediyl-bisoxy]-11β-[4-(N,N-diethylamino)-phenyl]-17α-(prop-1-ynyl)-Δ[9]-estrene-5α,17β-diol with a specific rotation of $[\alpha]_D^{20} = -61° \pm 2.5°$ (c=0.7% in CHCl₃).

STEP C:
11β-[4-(N,N-diethylamino)-phenyl]-17α-(prop-1-ynyl)-Δ⁴,⁹-estradiene-17β-ol-3-one A mixture of 8 ml of 2N hydrochloric acid, 3.12 g of the product of Step B and 45 ml of methanol was stirred at 20° C. under an inert atmosphere for 45 minutes and was then poured into water. The mixture was neutralized by addition of 2N sodium hydroxide solution and was extracted with methylene chloride. The organic phase was dried and evaporated to dryness and the residue was chromatographed over silica gel. Elution with a 1-1 benzene-ethyl acetate mixture yielde 1.34 g of 11β-[4-(N,N-diethylamino)-phenyl]-17α-(prop-1-yny)-Δ⁴,⁹-estradiene-17β-ol-3-one with a specific rotation of $[\alpha]_D^{20} = +144.5° \pm 3°$ (c=0.8% in chloroform).

Analysis: $C_{31}H_{39}NO_2$; molecular weight=457.63
Calculated: %C 81.36; %H 8.59; %N 3.06; Found: %C 81.7, %H 8.8; %N 2.09.

EXAMPLE 27

11β-[4-(N-methyl-N-3-methylbutylamino)-phenyl]-17α-(prop-1-ynyl)-Δ⁴,⁹-estradiene-17β-ol-3-one STEP A: N-methyl-N-(3-methylbutyl)-aniline 121 g of isoamyl bromide were added dropwise to a mixture of 86 g of N-methyl-aniline, 500 ml of anhydrous benzene and 81 g of anhydrous triethylamine and the mixture was refluxed for 100 hours and was filtered. The filtrate was washed with water, dried and evaporated to dryness. The residue was distilled to obtain 90 g of N-methyl-N-(3-methylbutyl)-aniline boiling at 132° C. at 18 mm Hg.

STEP B: N-methyl-N-(3-methylbutyl)-4-bromo-aniline

A solution of 58 g of bromine in 60 ml of acetic acid was added dropwise at about 15° C. over one hour to a mixture of 64 g of the product of Step A in 300 ml of acetic acid and the mixture was stirred at 80° C. for 8 hours and was poured into iced water. The mixture was extracted with methylene chloride and the organic phase was washed with aqueous sodium bicarbonate, with water, dried and evaporated to dryness. The residue was distilled to obtain 70 g of N-methyl-N-(3-methylbutyl)-4-bromo-aniline boiling at 119° C. at 0.5 mm Hg.

STEP C:
3,3-[1,2-ethanediyl-bisoxy]-11β-[4-(N-methyl-N-3-methylbutylamino)-phenyl]-17α-(prop-1-ynyl)-Δ⁹-estrene-5α,17β-diol A few ml of a solution of the product of Step B in tetrahydrofuran were added under an inert atmosphere to a mixture of 4.12 g of magnesium and 10 ml of tetrahydrofuran and the reaction was started by addition of 0.2 ml of 1,2-dibromoethane. The rest of the solution of the product of Step B in anhydrous tetrahydrofuran (32.6 g in 90 ml) was added over 40 minutes to the mixture and after the temperature returned to room temperature, the mixture was stirred for one hour to obtain a 0.9M magnesium solution. A mixture of 3.77 g of copper chloride, 8 g of 3,3-[1,2-ethanediyl-bisoxy]-5α, 10α-epxoy-17α-(prop-1-ynyl)-Δ⁹⁽¹¹⁾-estrene-17β-ol and 90 ml anhydrous tetrahydrofuran was stirred under an inert atmosphere at 5° C. for 20 minutes and then 100 ml of the magnesium solution were added thereto. The mixture was poured into aqueous ammonium chloride solution and was extracted with ether containing triethylamine and then with methylene chloride containing triethylamine. The combined organic phases were washed with aqueous saturated sodium chloride solution, dried and evaporated to dryness to obtain 31.2 g of 3,3-[1,2-ethanediyl-bisoxy]-11β-[4-(N-methyl-N-3-methylbutylamino)-phenyl]-17α-(prop-1-ynyl)-Δ⁹-estrene-5α,17β-diol which was used as is for the next step. A sample of the product was chromatographed over silica gel and was eluted with a 96.5-4.5-0.5 methylene chloride-acetone-triethylamine mixture to obtain the compound with a specific rotation of $[\alpha]_D^{20} = -59.5° \pm 2.5°$ (c=0.7% in chloroform).

STEP D:
11β-[4-(N-methyl-N-(3-methyl-butyl)-amino)-phenyl]-17α-(prop-1-ynyl)-Δ⁴,⁹-estradiene-17β-ol-3-one A mixture of 52 ml of 2N hydrochloric acid, 26 g of the product of Step C and 200 ml of methanol was stirred for one hour and was then poured into aqueous sodium bicarbonate. The mixture was extracted with ether and then methylene chloride and the combined organic phases were washed with aqueous saturated sodium chloride solution, dried and evaporated to dryness. The residue was chromatographed over silica gel and was eluted with an 92-8 toluene-ethyl acetate mixture to obtain 3.23 g of 11β-[4-(N-methyl-N-(3-methyl-butyl)-amino)phenyl]-17α-(prop-1-ynyl)-Δ⁴,⁹-estradiene-17β-ol-3-one with a specific rotation of $[\alpha]_D^{20} = +125° \pm 3.5°$ (c=0.6% in chloroform).

Analysis: $C_{33}H_{43}NO_2$; molecular weight=485.71
Calculated: %C 81.6; %H 8.92; %N 2.88; Found: %C 81.4 %H 9.0; %N 2.7.

EXAMPLE 28

11β-[4-(N,N-dimethylaminoethylthio)-phenyl]-17α-(prop-1-ynyl)-Δ⁴,⁹-estradiene-17β-ol-3-one

STEP A:
4-(N,N-dimethylaminoethylthio)-bromobenzene

A solution of 23.5 g of chloroethyldimethylamine.HCl in 75 ml of ethanol was added to 160 ml of sodium hydroxide solution formed by dissolving 20 g of sodium hydroxide pastilles in 500 ml of ethanol. A solution of 30 g of 4-bromothiophenol in 100 ml of ethanol was added to 160 ml of the said sodium hydroxide solution and the first solution was added thereto over 2 minutes at 20° C. The mixture was refluxed for 3 hours and was evaporated to dryness. Water was added to the residue and the mixture was extracted with methylene chloride. The organic phase was washed with aqueous 0.1N sodium hydroxide solution, then with water, dried and evaporated to dryness. The residue was distilled to obtain 35.5 g of 4-(N,N-dimethylaminoethylthio)-bromobenzene boiling at 110° C. at 0.1 mm Hg.

STEP B:
3,3-[1,2-ethanediyl-bisoxy]-11β-[4-(N,N-dimethylaminoethylthio)-phenyl]-17α-(prop-1-ynyl)-Δ⁹-estrene-5α,17β-diol A solution of 20 g of the product of Step A in 40 ml of anhydrous tetrahydrofuran was added over 45 minutes under an inert atmosphere to a mixture of 2 g of magnesium and 15 ml of tetrahydrofuran while the temperature rose to 56° C. and the reaction was started by addition of 1,2-dibromoethane. The mixture was returned to 20° C. and was stirred at 20° C. for 45 minutes under an inert atmosphere to obtain a 1.05M magnesium solution.

1.730 g of copper chloride were added with stirring at −20° C. under an inert atmosphere to 38 ml of the said magnesium solution and the mixture was stirred for 20 minutes. A solution of 5 g of 3,3-[1,2-ethanediyl-bisoxy]-5α,10α-epoxy-17α-(prop-1-ynyl)-$\Delta^{9(11)}$-estrene-17β-ol in 50 ml of anhydrous tetrahydrofuran was added to the mixture which was then stirred for 24 hours under an inert atmosphere at 20° C. and was then poured into 600 ml of iced water containing 60 g of ammonium chloride. The decanted aqueous phase was extracted with diethyl oxide containing triethylamine and the combined organic phase was washed with aqueous saturated sodium chloride solution, dried and evaporated to dryness. The residue was chromatographed over silica gel and was eluted with a 95-5 methylene chloride-acetone mixture to obtain 10.3 g of 3,3-[1,2-ethanediyl-bisoxy]-11β-[4-(N,N-dimethylaminoethylthio)-phenyl]-17α-(prop-1-ynyl)-$\Delta^9$-estrene-5α,17β-diol.

IR Spectrum: Absorption at 3600 cm$^{-1}$ (OH); at 2240 cm$^{-1}$ (C≡C); at 1705 and 1670 cm$^{-1}$ (CO and conjugated CO); at 1615 and 1490 cm$^{-1}$ (aromatic bands).

STEP C:

11β-[4-(N,N-dimethylaminoethylthio)-phenyl]-17α-(prop-1-ynyl)-$\Delta^{4,9}$-estradiene-17β-ol-3-one A mixture of 20.6 ml of 2N hydrochloric acid, 10.3 g of the product of Step B and 72 ml of methanol was stirred at 20° C. under an inert atmosphere for 25 minutes and was neutralized by addition of aqueous saturated sodium bicarbonate solution. 200 ml of diethyl oxide were added to the mixture and the decanted aqueous phase was extracted with diethyl oxide. The combined organic phases were washed with aqueous saturated sodium chloride solution, dried and evaporated to dryness and the residue was chromatographed over silica gel. Elution with a 9-1 methylene chloride-methanol mixture yielded 3 g of 11β-[4-(N,N-dimethylaminoethylthio)-phenyl]-17α-(prop-1-ynyl)-$\Delta^{4,9}$-estradiene-17β-ol-3-one which after crystallization by empasting with diisopropyl oxide melted at 145° C. and had a specific rotation of $[\alpha]_D^{20} = +125° \pm 2°$ (c=1% in chloroform).

EXAMPLE 29

11β-[4-(N,N-dimethylamino)-phenyl]-21-trimethylsilyl-19-nor-17α-$\Delta^{4,9}$-pregnadiene-20-yne-17β-ol-3-one

STEP A:

3,3-[1,2-ethanediyl-bisoxy]-11β-[4-(N,N-dimethylamino)-phenyl]-21-trimethylsilyl-19-nor-17α-$\Delta^9$-pregnene-20-yne-5α,17β-diol A mixture of 13 ml of a 1.6M ethyl magnesium bromide in tetrahydrofuran and 13 ml of anhydrous tetrahydrofuran was stirred for 5 minutes at 0° to 5° C. and 3.4 ml of trimethylsilyl acetylene were added thereto dropwise. The temperature was allowed to rise to 20° C. and the mixture was then stirred for 20 minutes. Then, a solution of 1.12 g of the product of Step B of Example 7 in 10 ml of anhydrous tetrahydrofuran was added dropwise to the mixture and the mixture was stirred at room temperature for 16 hours and was poured into aqueous ammonium chloride solution. The mixture was stirred at room temperature for 10 minutes and was extracted with methylene chloride. The organic phase was washed with aqueous saturated sodium chloride solution, was dried and evaporated to dryness. The residue was chromatographed over silica gel and was eluted with a 6-4 petroleum ether-ethyl acetate mixture to obtain 680 mg of 3,3-[1,2-ethanediyl-bisoxy]-11β-[4-(N,N-dimethylamino)-phenyl]-21-trimethylsilyl-19-nor-17α-$\Delta^9$-pregnene-20-yne-5α,17β-diol with a specific rotation of $[\alpha]_D^{20} = -76.5° \pm 3°$ (c=0.5% in chloroform).

STEP B:

11β-[4-(N,N-dimethylamino)-phenyl]-21-trimethylsilyl-19-nor-17α-$\Delta^{4,9}$-pregnadiene-20-yne-17β-ol-3-one A mixture of 1 ml of 2N hydrochloric acid, 562 mg of the product of Step A and 15 ml of methanol was stirred at room temperature for 40 minutes and was poured into aqueous sodium bicarbonate solution. The mixture was extracted with ether and the organic phase was washed with aqueous saturated sodium chloride solution, was dried and evaporated to dryness. The residue was chromatographed over silica gel and was eluted with a 6-4 petroleum ether-ethyl acetate mixture to obtain 364 mg of 11β-[4-(N,N-dimethylamino)-phenyl]-21-trimethylsilyl-19-nor-17α-$\Delta^{4,9}$-pregnadiene-20-yne-17β-ol-3-one with a specific rotation of $[\alpha]_D^{20} = +97.5° \pm 3°$ (c=0.35% in CHCl$_3$).

Analysis: $C_{31}H_{41}NO_2Si$; molecular weight=487.76 Calculated: %C 76.33; %H 8.47; %N 2.87; Found: %C 76.4 %H 8.7; %N 2.8.

EXAMPLE 30

N-oxide of 11β-[4-(N,N-dimethylaminomethyl)-phenyl]-17α-(prop-1-ynyl)]-$\Delta^{4,9}$-estradiene-17β-ol-3-one A solution of 0.64 g of m-chloroperbenzoic acid in 12.8 ml of methylene chloride was added over 15 minutes at 0° to 5° C. to a solution of 1.4 g of the product of Example 23 in 28 ml of methylene chloride and the mixture was stirred at 0° to 5° C. for one hour and was then poured into aqueous 0.2N sodium thiosulfate solution. The decanted aqueous phase was extracted with methylene chloride and the organic phase was washed with aqueous sodium bicarbonate solution, dried and evaporated to dryness. The residue was chromatographed over silica gel and was eluted with an 8-2 mixture to obtain 1.28 g of N-oxide of 11β-[4-(N,N-dimethylaminomethyl)-phenyl]-17α-(prop-1-ynyl)-$\Delta^{4,9}$-estradiene-17β-ol-3-one. The product was dissolved in a mixture of methylene chloride and diisopropyl oxide and the mixture was vacuum filtered to obtain 1.075 g of the said product melting at 215° C. and having a specific rotation of $[\alpha]_D^{20} = +74.5° \pm 2.5°$ (c=0.7% in CHCl$_3$).

EXAMPLE 31

Hemifumarate of 11β-[4-(N,N-dimethylaminomethyl)-phenyl]-17α-(prop-1-ynyl)-$\Delta^{4,9}$-estradiene-17β-ol-3-one A mixture of 0.378 g of fumaric acid in 4.54 ml of ethanol was added to a mixture of 1.44 g of the product of Example 23 in 2.88 ml of ethanol and the mixture was stirred at 60° C. for 30 minutes. The mixture returned to 20° C. and was stirred. The mixture was evaporated to dryness and the residue was taken up in ether. The mixture was vacuum filtered and the product was dried to obtain 1.70 g of hemifumarate of 11β-[4-(N,N-dimethylaminomethyl)-phenyl]-17α-(prop-1-ynyl)-$\Delta^{4,9}$-estradiene-17β-ol-3-one melting at 160° C. and having a specific rotation of $[\alpha]_D^{20} = +70.5° \pm 2.5°$ (c=0.8% in CHCl$_3$).

EXAMPLE 32

11β-[4-(N,N-dipropylamino)-phenyl]-17α-(prop-1-ynyl)-Δ$^{4,9}$-estradiene-17β-ol-3-one

STEP A:

3,3-[1,2-ethanediyl-bisoxy]-11β-[4-(N,N-dipropylamino)-phenyl]-17α-(prop-1-ynyl)-Δ$^9$-estrene-5α,17β-diol A solution of 52 g of 4-bromo-N,N-dipropyl-aniline in 110 ml of tetrahydrofuran was added dropwise at 40° C. under an inert atmosphere to a mixture of 5 g of magnesium and 15 ml of anhydrous tetrahydrofuran to obtain a 1.1M magnesium solution. A solution of 5.55 g of 3,3-[1,2-ethanediyl-bisoxy]-5α,10α-epoxy-17α-(prop-1-ynyl)-Δ$^{9(11)}$-estrene-17β-ol and 200 mg of cuprous chloride was stirred at 0° to 5° C. and then 50 ml of the magnesium solution were added thereto over 15 minutes. The mixture was stirred at 20° C. for one hour and was then poured into aqueous saturated ammonium chloride solution. The mixture was extracted with ether and the organic phase was dried and evaporated to dryness. The residue was chromatographed over silica gel and was eluted with a 7-3 toluene-ethyl acetate mixture to obtain 6.3 g of 3,3-[1,2-ethanediyl-bisoxy]-11β-[4-(N,N-dipropylamino)-17α-(prop-1-ynyl)-Δ$^9$-estrene-5α, 17β-diol with a specific rotation of $[\alpha]^{20} = -56° \pm 2°$ (c=0.8% in CHCl$_3$).

Analysis: C$_{35}$H$_{49}$NO$_4$; molecular weight=547.75
Calculated: %C 76.74; %H 9.02; %N 2.56; Found: %C 76.6; %H 9.2; %N 2.5.

STEP B:

11β-[4-(N,N-dipropylamino)-phenyl]-17α-(prop-1-ynyl)-Δ$^{4,9}$-estradiene-17β-ol-3-one A mixture of 10 ml of 2N hydrochloric acid, 5.83 g of the product of Step A and 80 ml of methanol was stirred at 20° C. for 50 minutes and was then neutralized by addition of N sodium hydroxide solution. The mixture was evaporated to dryness under reduced pressure and the residue was taken up in methylene chloride. The organic phase was washed with water, dried and evaporated to dryness and the residue was chromatographed over silica gel. Elution with a 3-1 toluene-ethyl acetate mixture yielded 3.81 g of 11β-[4-(N,N-dipropylamino)-phenyl]-17α-(prop-1-ynyl)-Δ$^{4,9}$-estradiene-17β-ol-3-one.

IR Spectrum:

Absorption at 3600 cm$^{-1}$ (OH); at 1654 cm$^{-1}$ (C=O); at 1610-1595-1558 and 1517 cm$^{-1}$ (Δ$^{4,9}$ and aromatic bands); at 2240 cm$^{-1}$ (C≡C).

The following products were prepared by the process of the invention using the appropriate starting materials:

(A) 11β-[4-(N-ethyl-N-methylamino)-phenyl]-17α-(prop-1-ynyl)-Δ$^{4,9}$-estradiene-17β-ol-3-one melting at 174° C. and having a specific rotation of $[\alpha]_D^{20} = +149° \pm 2.5°$ (c=1% in CHCl$_3$).

(B) 11β-[N-methyl-2,3-dihydro-1H-indol-5-yl]-17α-(prop-1-ynyl)-Δ$^{4,9}$-estradiene-17β-ol-3-one melting at 176° C. and having a specific rotation of $[\alpha]_D^{20} = +133° \pm 3°$ (c=0.8% in CHCl$_3$).

(C) 3-hydroxyimino-11β-[4-(N,N-dimethylamino)-phenyl]-17α-(prop-1-ynyl)-Δ$^{4,9}$-estradiene-17β-ol (Z isomer) melting at 260° C. and having a specific rotation of $[\alpha]_D^{20} = +141° \pm 3.5°$ (c=0.8% in CHCl$_3$) and the corresponding E isomer melting a 220° C. and having a specific rotation of $[\alpha]_D^{20} = +164° \pm 3.5°$ (c=0.8% in CHCl$_3$).

(D) N-oxide of 11β-[4-pyrrolidyl-phenyl]-17α-(prop-1-ynyl)-Δ$^{4,9}$-estradiene-17β-ol-3-one melting at 220° C. and having a specific rotation of $[\alpha]_D^{20} = +88° \pm 2.5°$ (c=0.75% in CHCl$_3$ (E) 11β-[4-(N-methyl-N-isopropylamino)-phenyl]-17α-(prop-1-ynyl)-Δ$^{4,9}$-estradiene-17β-ol-3-one with a specific rotation of $[\alpha]_D^{20} = +140° \pm 3.5°$ (c=0.5% in CHCl$_3$).

(F) N-oxide of 11β-[4-(N,N-dimethylaminoethoxy)-phenyl]-17α-(prop-1-ynyl)-Δ$^{4,9}$-estradiene-17β-ol-3-one with a specific rotation of $[\alpha]_D^{20} = +60.5°$ (c=1.2% in CHCl$_3$).

(G) N-oxide of 11β-[(N-methyl-2,3-dihydro-1H-indol-5-yl]-17α-(prop-1-ynyl)-Δ$^{4,9}$-estradiene-17β-ol-3-one with a specific rotation of $[\alpha]_D^{20} = +103° \pm 2.5°$ (C=0.8% in CHCl$_3$).

(H) 11β-[4-(N-methyl-N-trimethylsilylmethylamino)-phenyl]-17α-(prop-1-ynyl)-Δ$^{4,9}$-estradiene-17β-ol-3-one.

(I) 11β-[4-(N-methyl-N-dimethylaminoethylamino)-phenyl]-17α-(prop-1-ynyl)-Δ$^{4,9}$-estradiene-17β-ol-3-one.

(J) 11β-[4-(N-methyl-piperazin-1-yl)-phenyl]-17α-(prop-1-ynyl)-Δ$^{4,9}$-estradiene-17β-ol-3-one.

(K) 11β-[4-(N,N-dimethylamino)-phenyl]-17-hydroxyimino-Δ$^{4,9}$-estradiene-3-one with a specific rotation of $[\alpha]_D^{20} = +207.5° \pm 3.5°$ (c=1% in CHCl$_3$).

(L) 3(E)-hydroxyimino-11β-[4-(N,N-dimethylamino)-phenyl]-17-hydroxyimino-Δ$^{4,9}$-estradiene-3-one with a specific rotation of $[\alpha]_D^{20} = +195° \pm 3°$ (c=1% in CHCl$_3$) and its corresponding 3(Z) isomer with a specific rotation of $[\alpha]_D^{20} = +163° \pm 2.5°$ (c=0.6% in CHCl$_3$).

EXAMPLE 33

Tablets were prepared containing 50 mg of the product of Example 4 and sufficient excipient of talc, starch and magnesium stearate for a final tablet weight of 120 mg.

PHARMACOLOGICAL STUDY

I. Activity of products on hormonal receptors

A. Mineralcorticoidal receptor of kidneys of the rat

Male Sprague-Dawley EOPS rats weighing 140 to 160 g were surrenalectomized 4 to 8 days previously were killed and their kidneys were perfused in situ with 50 ml of a buffer (10 mM of Tris 0.25M of Saccharose and sufficient hydrochloric acid for a pH of 7.4). The kidneys were then removed, decapsulated and homogenized at 0° C. with of a polytetrafluoroethylene-glass Potter (1 g of tissue per 3 ml of buffer). The homogenate was centrifuged for 10 minutes at 800 g at 0° C.

After elimination of the fixation of tritiated aldosterone with glucocorticoid receptor, 21-methyl-Δ$^{1,4,6}$-pregnatrien-20-yne-11β,17β-diol-3-one fixed only with the glucocorticoid receptor was added to the surnageant at a final concentration of 10$^{-6}$M. The surnageant was ultracentrifuged at 105,000 g for 60 minutes at 0° C. and aliquoits of the resulting surnageant were incubated at 0° C. with a constant concentration (T) of tritiated aldosterone in the presence of increasing concentrations (0–2500×10$^{-9}$M) of cold aldosterone or the cold test product. After a time (t) of incubation, the concentration of tied tritied aldosterone (B) was measured by the technique of adsorption on carbon-dextran.

B. Androgen receptor of prostate of rats

Male Sprague-Dawley EOPS rats weighing 160 to 200 g were castrated and 24 hours later, the animals were killed. The prostates were removed, weighed and homogenized at 0° C. with a polytetrafluoroethylene-glass Potter with a buffered TS solution (Tris, 10 mM, 0.25M Saccharose, HCl-pH of 7.4) using 1 g of tissue per 5 ml of TS. The homogenate was then ultracentrifuged at 105,000 g after 60 minutes at 0° C. and aliquoits of the resulting supernatant were incubated at 0° C. for 2 hours with a constant concentration (T) of product P or 17α-methyl-$\Delta^{4,9,11}$-estratiene-17β-ol-3-one in the presence of increasing concentrations $(0-1,000 \times 10^{-9}M)$ of either cold P, cold testosterone or the test compound. The concentration of tied tritiated P (B) was measured for each incubate by the technique of adsorption on carbon-dextran.

C. Progestogen receptor of the uterus of rabbits

Immature rabbits weighing about 1 kg received a cutaneous application of 25 μg of estradiol and the animals were killed 5 days later. The uterus were removed, weighed and homogenized at 0° C. with a polytetrafluoroethylene-glass Potter in a buffered TS solution [Tris 10 mM, 0.25M of Saccharose, HCl-pH of 7.4] with 1 g of tissue per 50 ml of TS. The homogenate was ultracentrifuged at 105,000 g for 90 minutes at 0° C. and aliquoits of the resulting supernatant were incubated at 0° C. for a time (t) with a constant concentration (T) of tritiated product R or 17,21-dimethyl-19-nor-$\Delta^{4,9}$-pregnadiene-3,20-dione in the presence of increasing concentrations $(0$ to $2500 \times 10^{-9}M)$ of either cold R, cold progesterone or cold test compound. The concentration of tied tritiated R (B) was then measured for each incubate by the technique of adsorption on carbon-dextran.

D. Gluocorticoid receptor of thymus of rats

Male Sprague-Dawley EOPS rats weighing 160 to 200 g were surrenalectomized and the animals were killed 4 to 8 days later. The thymus were removed and homogenized at 0° C. in a buffered TS solution of 10 mM Tris, 0.25M of Saccharose, 2 mM of dithiothreitol, HCl for a pH of 7.4 using a polytetrafluoroethylene-glass Potter at a rate of 1 g of tissue per 10 ml of TS. The homogenate was ultracentrifuged at 105,000 g for 90 minutes at 0° C. and aliquoats of the resulting supernatant were incubated at 0° C. for a time (t) with a constant concentration (T) of tritiated dexamethasone in the presence of an increasing concentration $(0$ to $2500 \times 10^{-9}M)$ of either cold dexamethasone or cold test product. The concentration of tiedtritiateddexamethasone (B) was measured for each incubate by the the adsorption on carbon-dextran technique.

E. Estrogen receptor of uterus of mice

Immature female mice 18 to 21 days old were killed and the uterus removed and homogenized at 0° C. with a polytetrafluoroethylene-glass Potter in a buffered TS solution consisting of 10 mM Tris, 0.25M saccharose, HCl for a pH of 7.4 at a rate of 1 g of tissue per 25 ml of TS. The homogenate was then ultracentrifuged at 105,000 a for 90 minutes at 0° C. and aliquoits of the resulting tritiated were incubated at 0° C. for a time (t) with a constant concentration (T) of tritied estradiol in the presence of increasing concentrations $(0$ to $1000 \times 10^{-9}M)$ of either cold estradiol or cold test compound. The concentration of tiedtritiatedestradiol (B) was measured for each incubate by the technique of adsorption on carbon-dextran.

The calculation of the relative affinity of concentration (ARL) was identical for all of the above receptor tests. One traced the following two curves: the percentage of tiedtritiated hormone B/T as a function of the logarithm of the cold hormone concentration and B/T as a function of the logarithm of the concentration of the cold test product. One determined the line of the equation.

$$I_{50} = \frac{\frac{B}{T} \text{max.} + \frac{B}{T} \text{min.}}{2}$$

B/T max. is the percentage of tied tritiated hormone for an incubation of the hormone at concentration T B/T min. is the percentage of tiedtritiated hormone for an incubation of the tritiatedhormone at a concentration (T) in the presence of a large excess of cold hormone $(2500 \times 10^{-9}M)$.

The intersection of the $I_{50}$ line and the curves permits one to determine the concentrations of the cold hormone of the reference (CH) and the cold test compound (CX) which inhibit by 50% the tieing of tritiatedhormone with the receptor. The relative affinity of tieing (ARL) of the test product was determined by the equation:

$$ARL = 100 \times \frac{CH}{CX}$$

The results are reported in the following Tables.

| Time of incubation at 0° C. | Mineralo corticoid | | | Androgen | | | Progestogen | | | Gluco- corticoid | | | Estrogen | | |
|---|---|---|---|---|---|---|---|---|---|---|---|---|---|---|---|
| | 2H | 4H | 24H | 2H | 4H | 24H | 2H | 4H | 24H | 2H | 4H | 24H | 2H | 4H | 24H |
| 4  | — | — | 0   | — | — | 20   | 74  | — | 640 | — | 270 | 265 | 0 | — | — |
| 17 | — | — | 0   | — | — | 68   | 81  | — | 351 | — | 279 | 235 | 0 | — | — |
| 14 | — | — | —   | — | — | 0    | 41  | — | 250 | — | 46  | 94  | 0 | — | — |
| 8  | — | — | 0   | — | — | 14.7 | 81  | — | 268 | — | 212 | 167 | 0 | — | — |
| 10 | — | — | 0   | — | — | 32   | 78  | — | 467 | — | 254 | 292 | 0 | — | — |
| 11 | — | — | 0   | — | — | 9.8  | 6.3 | — | 8.3 | — | 9   | 14  | 0 | — | — |
| 16 | — | — | 1.7 | — | — | 29   | 129 | — | 166 | — | 283 | 259 | 0 | — | — |
| 12 | — | — | 0   | — | — | 2.8  | 0.6 | — | 0.4 | — | 5.3 | 6.2 | 0 | — | — |
| 6  | — | — | 0.8 | — | — | 7.3  | 10  | — | 4.3 | — | 171 | 118 | 0 | — | — |
| 20 | — | — | —   | — | — | 2.2  | 1.1 | — | 2.5 | — | 7.8 | 5   | 0 | — | — |
| 22 | — | — | 0.3 | — | — | 8    | 175 | — | 843 | — | 178 | 221 | 0 | — | — |
| 29 | — | — | 0   | — | — | 4.6  | 15.2| — | 38  | — | 79  | 104 | 0 | — | — |

CONCLUSION

The tested compounds and especially those of Examples 4,10,16,17 and 22 present a very remarkable affinity for glucocorticoid and progestogen receptors as well as slight affinity for androgen receptors. On the contrary, the products do not have any activity for mineralorticoid and estrogen receptors. These results lead to the conclusion that the products present an agonist of antagonistic activity to glucocorticoids, progestogens and androgens.

II Anti-inflammatory Activity

The anti-inflammatory activity of the compound of example 4 was determined by the classical granuloma test by a modification of the Meier et al test [Experientia, Vol. 6 (1950), p. 469] in which normal female Wistar rats weighing 100 to 110 g received an implantation of 2 pellets of cotton weighing 10 mg each under the thorax skin. The subcutaneous treatment which began immediately after the implantation for 2 days was 3 injections per day. 16 hours after the last injection, the animals were killed and the pellets together with the granuloma tissue formed were weighed in the fresh state and after 16 hours at 60° C. The weight of the granuloma was obtained by subtracting the initial weight of the cotton. The thymus was also removed and weighted to determine the thymolytic activity of the test product.

At a subcutaneous dose of 50 mg/kg, the product of example 4 did not show any gluocorticoidal anti-inflammatory activity or thymolytic activity.

III Antiglucocorticoidal Activity

The test used was that of Daune et al [Molecular Pharmacology, Vol. 13 (1977), p. 948–955] entitled "The relationship between glucocorticoid structure and effects upon thymocytes" for mice thymocytes. The thymocytes of surrenalectomized rats were incubated at 7° C. for 3 hours in a nutritive medium containing $5 \times 10^{-8}M$ of dexamethasone in the presence or absence of the test compound at different concentrations. Tritied uridine was added and incubation was continued for one hour. The incubates were cooled and treated with a 5% trifluoroacetic acid solution and the mixture was filtered with Whatman GF/A paper. The filter was washed 3 times with a 5% trifluoroacetic acid solution and retained radioactivity on the filter was determined. Glucocorticoids, and especially dexamethasone provoked a lessening of incorporation of tritiadeduridine and the tested compounds, especially those of Examples 6,8,10,11,14,16,20 and 22, opposed this effect as can be seen from the following Table.

| Product of Example | $5 \cdot 10^{-8}$ Dexamethasone + Product tested | % of inhibition of effect of Dexamethasone |
|---|---|---|
| 4 | $10^{-8}M$ | 30 |
|  | $10^{-7}M$ | 70 |
|  | $10^{-6}M$ | 90 |
| 14 | $10^{-8}M$ | 18 |
|  | $10^{-7}M$ | 57 |
|  | $10^{-6}M$ | * |
| 8 | $10^{-8}M$ | 22 |
|  | $10^{-7}M$ | 53 |
|  | $10^{-6}M$ | * |
| 10 | $10^{-8}M$ | 57 |
|  | $10^{-7}M$ | 85 |
|  | $10^{-6}M$ | * |
| 11 | $10^{-8}M$ | 14 |
|  | $10^{-7}M$ | 34 |
|  | $10^{-6}M$ | 75 |
| 16 | $10^{-8}M$ | 28 |
|  | $10^{-7}M$ | 60 |
|  | $10^{-6}M$ | 99 |
| 6 | $10^{-8}M$ | 5 |
|  | $10^{-7}M$ | 15 |
|  | $10^{-6}M$ | 83 |
| 20 | $10^{-8}M$ | 4 |
|  | $10^{-7}M$ | 21 |
|  | $10^{-6}M$ | 50 |
| 22 | $10^{-8}M$ | 16 |
|  | $10^{-7}M$ | 69 |
|  | $10^{-6}M$ | * |

*A dose of $10^{-6}M$ inhibited totally the effect of dexamethasone

CONCLUSION

The products of the invention used alone do not provoke any effect of the glucocorticoid type and the tested products present a very remarkable antiglucocorticoid activity and are devoid of any glucocorticoid activity.

IV. PROGESTOMIMETIC AND ANTI-PROGESTOMIMETIC ACTIVITY (a) Groups of immature female rabbits weighing about 1 kg had administered to them sub-cutaneously from day 1 to day 5, 5 μg of estradiol. The product tested is afterward administered orally from day 8 to day 11 in a volume of 0.5 cm³ of water containing 0.5% of carboxymethyl cellulose and 0.2% of Tween. On day 12 the rabbits were sacrificed, their uteruses were retained and fixed in Bouin's solution and histologically studied.

The changes in the uterine endometrium were noted according to the method of McPhail. Only superior results or those equal to two units of McPhail were considered significant.

The following results were obtained.

| TREATMENT | DOSAGE mg/kg | CHANGE IN THE ENDOMETRIUM IN McPHAIL UNTS |
|---|---|---|
| Progesterone (subcutaneously) | 0.2 | 3.2 |
| Product of Example 4 (by mouth) (RU 38486 or RU 486) | 0.3 | 0 |
|  | 1.0 | 0 |
|  | 3.0 | 0 |
|  | 10.0 | 0 |
|  | 50 | 0 |
| Progesterone (subcutaneously) | 0.2 | 3.0 |
| Progesterone 0.2 mg (subcutaneously) + the compound of example 4 (by mouth) | 0.3 | 2.8 |
|  | 1 | 2.1 |
|  | 3 | 1.4 |
|  | 10 | 0.6 |
|  | 20 | 0 | b. Technique described by D. A. Macginty, L. P. Anderson, and N. B. McCullough Endocrin. 1939, 24, 829

Groups of three immature female rabbits weighing about 1 kg were topically treated on the dorsal skin with 25 μg of estradiol in 10 μl of ethanol on day 1. On day 4 the product to be tested dissolved in 0.1 ml. of sesame oil containing 5% benzyl alcohol was introduced into a part of the uterus isolated between two ligatures. On the sixth day the animals were sacrificed, their uteruses retained and fixed in Bouin's solution for histological examination. Changes in the uterine endometrium were noted after the method of McPhail.

The following results were obtained.

| TREATMENT | DOSE μg/RABBIT | CHANGE IN THE ENDOMETRIUM |
|---|---|---|
| Product of Example 4 | 30 | 0 |
|  | 500 | 0 |
| Progesterone | 10 | 2.7 |
| Progesterone 10 μg + Product of Example 4 | 1 | 1.6 |
|  | 3 | 1.3 |
|  | 10 | 1.0 |
|  | 30 | 0.6 |
|  | 90 | 0.6 |

Conclusion:

This product tested is devoid of progestomimetic activity while on the contrary it possesses a remarkable antiprogestomimetic activity.

V. ANTI-IMPLANTATION AND ABORTIVE ACTIVITIES IN FEMALE RATS

The first day of gestation is determined by the presence of sperm in the vagina. The product of example 4 is administered by mouth 3 consecutive days at the rate of 5 ml per kilogram as a suspension of 0.5% of carboxymethyl cellulose in water containing 0.2% Tween.

The animals were sacrificed between the 5th and 8th day after the last treatment and the uterus was examined.

The following results were obtained:

| DAYS OF TREATMENT | DOSE mg/kg/day | RESULTS |
|---|---|---|
| 1,2,3 | 10 | Non-implantation |
| " | 2 | No action |
| 4,5,6 | 10 | Non-implantation |
| " | 2 | Non-implantation |
| 7,8,9 | 10 | Abortion |
| " | 2 | Abortion |
| 10,11,12 | 10 | Abortion |
| " | 2 | Abortion |
| 13,14,15 | 10 | Abortion |
| " | 2 | Abortion in 50% of the animals |

Conclusion:

This product tested showed anti-implantation activity and abortive activity in the rat at all times of the period of gestation.

Various modifications of the products and methods of the invention may be made without departing from the spirit or scope thereof and it is to be understood that the invention is intended to be limited only as defined in the appended claims.

What we claim is:

1. A compound selected from the group consisting of 19-nor steroids and 19-nor-D-homo-steroids of the formula

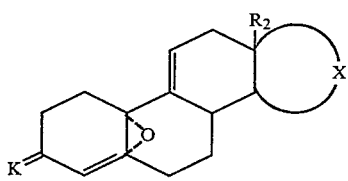

wherein $R_2$ is a hydrocarbon of 1 to 8 carbon atoms, X is selected from the group consisting of pentagonal ring and a hexagonal ring optionally substituted and optionally containing a double bond, and K is a ketone blocked in the form of a ketal, thioketal, oxime or methyloxime.

2. A compound of claim 1 wherein X is pentagonal ring.

3. A compound of claim 1 which is 3,3-(1,2-ethanediyl-bisoxy)-5α,10α-epoxy-17α-(prop-1-ynyl)-$\Delta^{9(11)}$-estrene-17β-ol.

4. A compound of claim 1 which is 3,3-dimethoxy-5α,10α-epoxy-17β-ethynyl-$\Delta^{9(11)}$-estrene-17β-ol.

5. A compound of claim 1 wherein X and the carbons to which it is attached form the ring of the formula

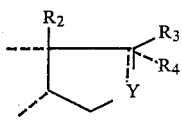

wherein $R_2$ has the above definition, the dotted line in the 16,17-position is an optional double bond, Y is

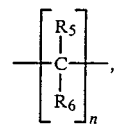

n is 1 or 2, $R_5$ is selected from the group consisting of hydrogen, alkyl of 1 to 8 carbon atoms, alkenyl and alkynyl of 2 to 8 carbon atoms, aryl of 6 to 14 carbon atoms and aralkyl of 7 to 15 carbon atoms, $R_6$ may be the same as $R_5$ and may be selected from the same group of members as $R_5$— or —OH, $R_3$ and $R_4$ are individually selected from the group consisting of hydrogen, —OH, —OAlK$_4$, —OCOAlK$_5$, alkenyl and alkynyl of 2 to 8 carbon atoms,

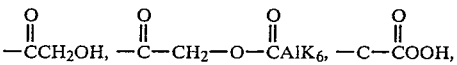

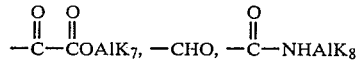

and —CN wherein AlK$_4$, AlK$_5$ and AlK$_8$ are selected from the group consisting of alkyl of 1 to 8 carbon atoms and aralkyl of 7 to 15 carbon atoms, AlK$_6$ is selected from the group consisting of optionally substituted alkyl of 1 to 8 carbon atoms and aralkyl of 7 to 15 carbon atoms and AlK$_7$ is alkyl of 1 to 8 carbon atoms and $R_3$ and $R_4$ form the group

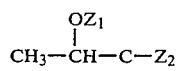

and $Z_1$ is selected from the group consisting of hydrogen, alkyl of 1 to 8 carbon atoms and acyl of an organic carboxylic acid of 1 to 8 carbon atoms and $Z_2$ is alkyl of 1 to 8 carbon atoms.

6. A compound of claim 5 wherein the D ring is saturated, $R_5$ and $R_6$ are hydrogen and n is 1.

7. A compound of claim 6 wherein $R_3$ is an OH group and $R_4$ is an alkynyl of 2 to 8 carbon atoms.

* * * * *